US012073560B2

(12) United States Patent
Madabhushi et al.

(10) Patent No.: US 12,073,560 B2
(45) Date of Patent: Aug. 27, 2024

(54) COMPUTATIONAL FEATURES OF TUMOR-INFILTRATING LYMPHOCYTE (TIL) ARCHITECTURE

(71) Applicants: Case Western Reserve University, Cleveland, OH (US); The United States Government as Represented by The Department of Veteran Affairs, Washington, DC (US); University of Pittsburgh—Of the Commonwealth System of Higher Education, Pittsburgh, PA (US)

(72) Inventors: Anant Madabhushi, Shaker Heights, OH (US); Sepideh Azarianpour Esfahani, Cleveland Heights, OH (US); Haider Mahdi, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 280 days.

(21) Appl. No.: 17/671,882

(22) Filed: Feb. 15, 2022

(65) Prior Publication Data
US 2022/0405918 A1 Dec. 22, 2022

Related U.S. Application Data

(60) Provisional application No. 63/212,231, filed on Jun. 18, 2021.

(51) Int. Cl.
G06T 7/00 (2017.01)
G06N 20/00 (2019.01)
(Continued)

(52) U.S. Cl.
CPC .......... G06T 7/0012 (2013.01); G06N 20/00 (2019.01); G06V 10/764 (2022.01);
(Continued)

(58) Field of Classification Search
CPC ........ G06T 7/0012; G06T 2207/30024; G06T 2207/30096; G06T 2207/20084;
(Continued)

(56) References Cited

U.S. PATENT DOCUMENTS

2017/0270666 A1* 9/2017 Barnes ............. G01N 33/57415
2019/0183429 A1* 6/2019 Sung .................... A61B 5/7267
(Continued)

Primary Examiner — Dhaval V Patel
(74) Attorney, Agent, or Firm — Eschweiler & Potashnik, LLC

(57) ABSTRACT

Various embodiments of the present disclosure are directed towards a method for generating a risk group classification for an African American (AA) patient. The method includes extracting a first plurality of architectural features from a digitized H&E slide image of the AA patient. A risk score for the AA patient is generated based on the first plurality of architectural features, where the risk score is prognostic of overall survival (OS) of the AA patient. The risk group classification is generated for the AA patient, where generating the risk group classification includes classifying the AA patient into either a high risk group or a low risk group based on the risk score, where the high risk group indicates the AA patient will die before a threshold date and the low risk group indicates the AA patient will die after or on the threshold date.

20 Claims, 17 Drawing Sheets

(51) Int. Cl.
  *G06V 10/764* (2022.01)
  *G06V 10/774* (2022.01)
  *G06V 20/69* (2022.01)
  *G16H 20/40* (2018.01)

(52) U.S. Cl.
  CPC .......... *G06V 10/774* (2022.01); *G06V 20/698* (2022.01); *G16H 20/40* (2018.01); *G06T 2207/30024* (2013.01); *G06T 2207/30096* (2013.01)

(58) Field of Classification Search
  CPC ............. G06T 2207/10016; G06T 7/12; G06T 2207/10024; G06T 7/143; G06T 2207/10056; G06T 2207/20072; G06T 7/149; G06T 2207/20081; G06T 2207/20104; G06T 2207/20152; G06N 20/00; G06N 20/10; G06V 10/764; G06V 10/774; G06V 20/698; G06V 20/695; G16H 20/40; G16H 20/10; G16H 30/40; G16H 50/30; G16H 50/20
  See application file for complete search history.

(56) References Cited

U.S. PATENT DOCUMENTS

| | | | |
|---|---|---|---|
| 2021/0090694 A1* | 3/2021 | Colley | G16H 15/00 |
| 2021/0110540 A1* | 4/2021 | Vaidya | G06N 20/20 |
| 2021/0110930 A1* | 4/2021 | Park | G16H 50/20 |

* cited by examiner

COMPUTATIONAL FEATURES OF TUMOR-INFILTRATING LYMPHOCYTE (TIL) ARCHITECTURE

REFERENCE TO RELATED APPLICATIONS

This application claims the benefit of U.S. Provisional Application No. 63/212,231 filed on Jun. 18, 2021, the contents of which are hereby incorporated by reference in their entirety.

FEDERAL FUNDING NOTICE

This invention was made with government support under CA199374, CA249992, CA202752, CA208236, CA216579, CA220581, CA239055, CA248226, CA254566, HL151277, EB028736, RR012463, and TR000254 awarded by the National Institutes of Health; and W81XWH-19-1-0668, W81XWH-15-1-0558, W81XWH-20-1-0851, W81XWH-18-1-0440, W81XWH-20-1-0595, and W81XWH-18-1-0404 awarded by the Department of Defense. The government has certain rights in the invention.

BACKGROUND

The uterus is a hollow organ, normally about a size and shape of a medium-sized pear. The uterus is where a fetus grows and develops when a woman is pregnant. The uterus comprises an outer layer known as the myometrium and an inner layer known as the endometrium. Endometrial cancer starts in cells of the inner layer (e.g., the endometrium) of the uterus.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Figure 1:
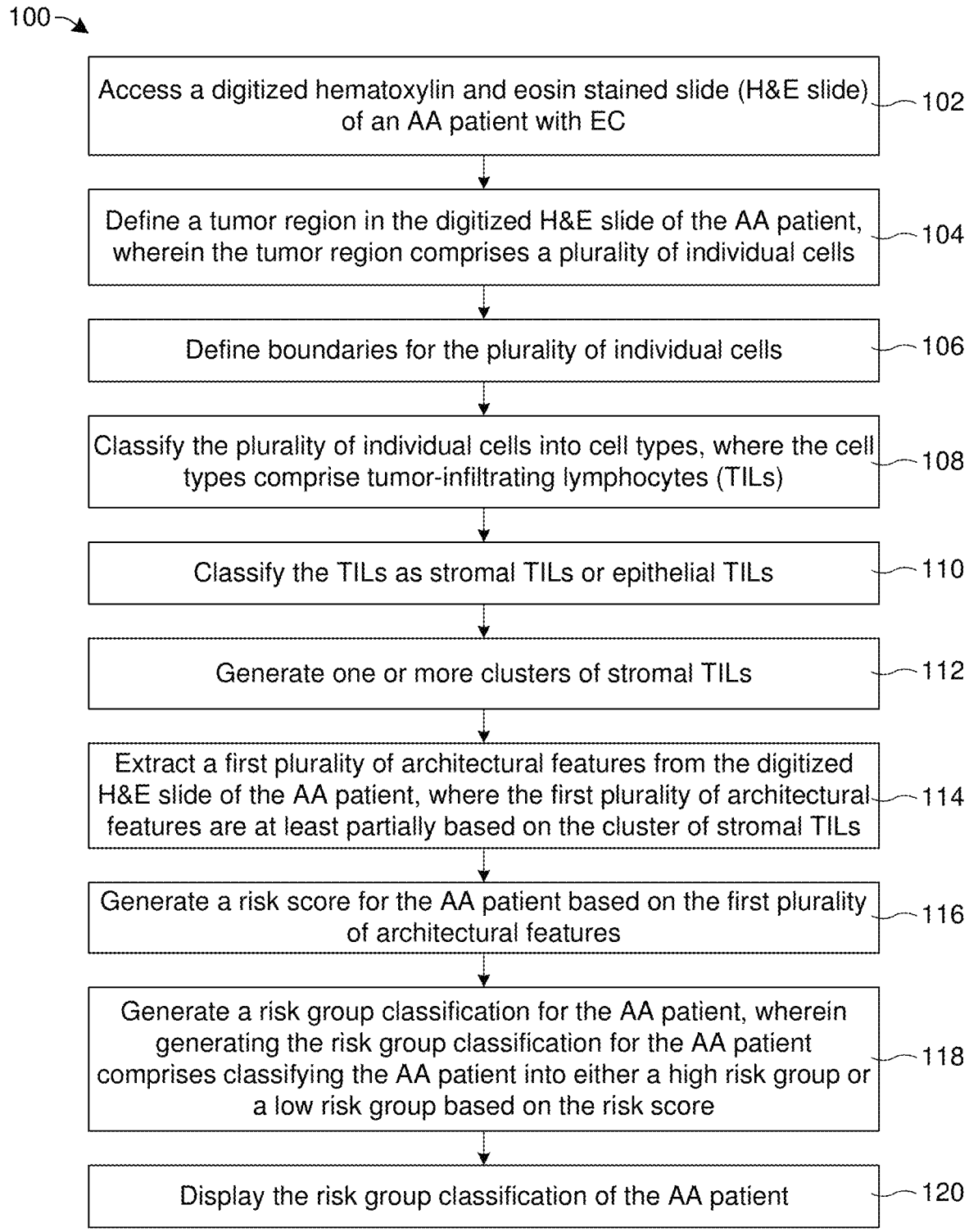
FIG. 1 illustrates some embodiments of a method for generating a prediction for overall survival (OS) of an African American (AA) patient with endometrial cancer (EC).

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Endometrial cancer (EC) is typically caught in early-stages and thus is treatable (e.g., with at least 85% 5-year overall survival (OS)) by surgery, chemotherapy, and/or radiotherapy. However, a fraction of EC cases are aggressive neoplasms such as high-grade or deeply invasive lesions (e.g., aggressive EC) and thus exhibit poor prognosis. It has been appreciated that EC may disproportionally affect different population groups (e.g., difference races, ethnicities, etc.). For example, African American (AA) women are disproportionately affected by high-grade EC than Caucasian American (CA) women, and thus AA women having EC may have a mortality rate that is approximately 80% higher than that of CA women having EC.

Various embodiments of the present disclosure relate to a method (and related apparatus) for determining prognostic features that are indicative of EC for different population groups (e.g., difference races, ethnicities, etc.). The method utilizes computational methods to identify prognostic features of architectural features of tumor-infiltrating lymphocytes (ArcTIL) from hematoxylin and eosin stained slides (H&E slides) of different population groups having EC. In some embodiments, the method may identify prognostic features of ArcTIL that are differentially prognostic of EC between population groups comprising AA and CA women.

Further, various embodiments of the present disclosure relate to a method (and related apparatus) that utilizes the prognostic features that are indicative of EC for AA women to prognosticate overall survival (OS) of AA women (and/or prognosticate a response to treatment (e.g., chemotherapy, radiotherapy, etc.) for the EC of the AA women). For example, the method may comprise accessing a digitized H&E slide image of an African American (AA) patient (e.g., AA woman), where the digitized H&E slide of the AA patient demonstrates tissue from a uterus of the AA patient and at least a portion of a gynecologic tumor. A tumor region is defined in the digitized H&E slide image of the AA patient, where the tumor region comprises at least a portion of the gynecologic tumor, and where the tumor region comprises a plurality of individual cells. The individual cells of the plurality of individual cells are then classified into cell types, where the cell types comprise tumor-infiltrating lymphocytes (TILs) and non-lymphocyte cells. The TILs are then classified as stromal TILs or epithelial TILs. A cluster of stromal TILs is generated (e.g., based on proximity of a subset of stromal TILs). A plurality of architectural features are extracted from the digitized H&E slide image of the AA patient. A risk score for the AA patient is generated based on the plurality of architectural features, where the risk score is prognostic of overall survival (OS) of the AA patient. A risk group classification is generated for the AA patient based on the risk score of the AA patient, where the risk group classification classifies the AA patient into either a high risk group (e.g., indicates the AA patient will die before a threshold date) or a low risk group (e.g., indicates the AA patient will die after or on the threshold date). By utilizing a risk score for an AA patient, which is prognostic of overall survival (OS) of the AA patient, and classifying the patient into a high risk group or a low risk group based on the risk score for the AA patient, treatment of the AA patient's EC may be accurately guided to achieve better treatment results (e.g., to utilize a more aggressive treatment(s) when the AA is classified into the high risk group and utilizing less aggressive treatment(s) when the AA is classified into the low risk group).

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations or methods described herein. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates some embodiments of a method 100 for generating a prediction for overall survival (OS) of an African American (AA) patient with endometrial cancer (EC). In some embodiments, the AA patient is referred to as a AA patient of interest (POI) (e.g., due to the method 100 generating a prediction of OS for the AA patient).

The method 100 comprises a first operation 102. At the first operation 102, a digitized hematoxylin and eosin stained slide (H&E slide) of an AA patient with EC is accessed. The digitized H&E slide image of the AA patient demonstrates one or more indicators of EC. The digitized H&E slide of the AA patient demonstrates tissue from the uterus of the AA patient and at least a portion of a gynecologic tumor. The portion of the gynecologic tumor demonstrated in the digitized H&E slide of the AA patient may be an indicator of EC.

In some embodiments, the gynecologic tumor is disposed in the endometrium of the uterus of the AA patient (e.g., demonstrated in the digitized H&E slide of the AA patient in the endometrium of the uterus of the AA patient) and/or the gynecologic tumor is a tumor that begin in the cells of the endometrium of the uterus of the AA patient (e.g., the gynecologic tumor is in a different location of the uterus but began in or metastasized from the endometrium of the uterus of the AA patient). In some embodiments, the digitized H&E slide of the AA patient is a digitized H&E slide of the AA patient that was taken before the start of a treatment plan for EC (e.g., chemotherapy, radiotherapy, hormone therapy, etc.).

The digitized H&E slide of the AA patient may be stored in memory, either locally or remotely. The digitized H&E slide of the AA patient may be obtained by an imaging device (e.g., a digital microscope). For example, in some embodiments, the digitized H&E slide of the AA patient may be digitized by scanning the H&E slide (e.g., the physical H&E slide) via an imaging system (e.g., the digital microscope). The digitized H&E slide may be captured and/or stored in a whole slide image file format. The digitized H&E slide of the AA patient may be obtained concurrently with the method 100 (e.g., via the imaging device implementing method 100) or prior to the method 100 (e.g., at a time that is before a time in which the method 100 is implemented). Accessing the digitized H&E slide of the AA patient includes acquiring electronic data, reading from a computer file, receiving a computer file, reading from a computer memory, or other computerized activity not practically performed in the human mind.

The method 100 comprises a second operation 104. At the second operation 104, a tumor region is defined in the digitized H&E slide of the AA patient. The tumor region comprises the portion of the gynecologic tumor. In some embodiments, defining the tumor region comprises defining an outer boundary of the portion of the gynecologic tumor. In some embodiments, the tumor region comprises the portion of the gynecologic tumor and a surrounding portion of tissue (e.g., a healthy portion of the endometrium of the uterus of the AA patient). The surrounding portion of tissue may extend around (completely or partially) the outer boundary of the portion of the gynecologic tumor. The surrounding portion of tissue may extend from (e.g., radially) the tumor region a predefined distance (e.g., 1 millimeter (mm), 2 mm, 3 mm, etc.).

Further, the tumor region comprises a plurality of individual cells. In other words, the portion of the gynecologic tumor (and the surrounding portion of tissue) are made up of the plurality of individual cells. The plurality of individual cells are demonstrated in the tumor region of the digitized H&E slide of the AA patient. The plurality of individual cells each have a specific cell type. For example, a first individual cell of the plurality of individual cells may be a tumor-infiltrating lymphocyte (TIL), a second individual cell of the plurality of individual cells may be a non-lymphocyte cells, a third individual cell of the plurality of individual cells may be a cancer cell, and so forth. Defining the tumor region in the digitized H&E slide of the AA patient includes acquiring electronic data, reading from a computer file, receiving a computer file, reading from a computer memory, or other computerized activity not practically performed in the human mind.

The method 100 comprises a third operation 106. At the third operation 106, boundaries for the plurality of individual cells are defined. In some embodiments, an outer boundary is defined for each of the plurality of individual cells. For example, an outer boundary for the first individual cell is defined, an outer boundary for the second individual cell is defined, and so forth. Defining the boundaries for the plurality of individual cells includes acquiring electronic data, reading from a computer file, receiving a computer file, reading from a computer memory, or other computerized activity not practically performed in the human mind.

The method 100 comprises a fourth operation 108. At the fourth operation 108, the plurality of individual cells are classified into cell types. In some embodiments, each of the plurality of individual cells is classified into its distinct cell type. The cell types comprise tumor-infiltrating lymphocytes (TILs), non-lymphocyte cells, cancer cells. For example, the first individual cell is classified as a TIL, the second individual cell is classified as a non-lymphocyte cells, the third individual cell is classified as a cancer cell, and so forth. The plurality of individual cells are classified into their respective cell types based on the physical structures of the plurality of individual cells demonstrated in the digitized H&E slide of the AA patient. It will be appreciated that the cell types may comprise other types of human cells. Classifying the plurality of individual cells are classified into cell types includes acquiring electronic data, reading from a computer file, receiving a computer file, reading from a computer memory, or other computerized activity not practically performed in the human mind The method 100 comprises a fifth operation 110. At the fifth operation 110, the TILs are classified as stromal TILs or epithelial TILs. For example, the first individual cell, which has been classified as a TIL, is one individual cell of a collection of individual cells of the plurality of individual cells. Each of the individual cells of the collection of individual cells have also been classified as TILs. The individual cells of the collection of individual cells are classified as stromal TILs or epithelial TILs. In some embodiments, the individual cells of the collection of individual cells may classified into other types of TILs. For example, in some embodiments, the TILs are classified as stromal TILs, epithelial TILs, and/or intratumoral TILs. More specifically, in some embodiments, the TILs are classified as stromal TILs or intratumoral TILs.

In some embodiments, an individual cell of the collection of individual cells (e.g., an individual TIL) may be classified (e.g., via a previously trained deep-learning algorithm) as a stromal TIL or an epithelial TIL by, first, defining a stroma (e.g., stromal region) and an epithelium (e.g., epithelial region) of the digitized H&E slide of the AA patient (or the tumor region). The individual cell of the collection of individual cells may be classified as a stromal TIL if the coordinates of the centroid of the individual cell of the collection of individual cells is within the stroma. On the other hand, if the coordinates of the centroid of the individual cell of the collection of individual cells is within the epithelium, the individual cell of the collection of individual cells is defined as an epithelial TIL. Classifying the TILs into either stromal TILs or epithelial TILs includes acquiring electronic data, reading from a computer file, receiving a computer file, reading from a computer memory, or other computerized activity not practically performed in the human mind.

In some embodiments, a histologist may define the tumor region (see, e.g., second operation 104), define the boundaries of the plurality of individual cells (see, e.g., third operation 106), classify the plurality of individual cells into their cell types (see, e.g., fourth operation 108), and/or classify the TILs as either stromal TILs or epithelial TILs (see, e.g., fifth operation 110). In other words, the histologist may performed one or more of the second operation 104, the third operation 106, the fourth operation 108, and the fifth operation 110.

In other embodiments, the tumor region and/or the boundaries of the plurality of individual cells may be defined (e.g., generated) by an image segmentation technique, such as, a watershed segmentation technique, a region growing technique, an active contour technique, a convolutional neural network (CNN), support vector machine (SVM) classifiers, some other image segmentation technique, or a combination of the foregoing. It will be appreciated that the tumor region and/or the boundaries of the plurality of individual cells may be generated using other image segmentations techniques.

In some embodiments, the image segmentation technique may also classify the plurality of individual cells into their cell types and/or classify the TILs as either stromal TILs or epithelial TILs. In other words, the image segmentation technique may perform one or more of the second operation 104, the third operation 106, the fourth operation 108, and the fifth operation 110.

In some embodiments, the image segmentation technique comprises processing a whole slide image of the digitized H&E slide of the AA patient at 10 times (10X) magnification. The image segmentation technique may be trained to define the tumor region (see, e.g., second operation 104), define the boundaries of the plurality of individual cells (see, e.g., third operation 106), classify the plurality of individual cells into their cell types (see, e.g., fourth operation 108), and/or classify the TILs as either stromal TILs or epithelial TILs (see, e.g., fifth operation 110). The image segmentation technique may be trained on different types of tissue images (e.g., estrogen receptor positive breast cancer tissue image patches) or the same type of tissue images (e.g., digitized H&E slides of the uterus of other patients with EC). In some embodiments, the image segmentation technique assigns a value to each pixel of the digitized H&E slide of the AA patient. The value that is assigned to each pixel reflects the likelihood such a pixel is part of the epithelium of the AA patient. In further embodiments, this probabilistic epithelial mask is converted to a binary mask by a likelihood threshold. Thus, the image segmentation technique may perform one or more of the second operation 104, the third operation 106, the fourth operation 108, and the fifth operation 110.

It will be appreciated that a combination of image segmentation techniques may be utilized to performed one or more of the second operation 104, the third operation 106, the fourth operation 108, and the fifth operation 110. For example, in some embodiments, a watershed image segmentation technique may be utilized to segment the nuclei of the plurality of individual cells (e.g., the second operation 104 and/or the third operation 106). A SVM classifier then uses shape, texture, and/or color features of the nuclei to classify the plurality of individual cells into their respective cell types (see, e.g., fourth operation 108) and/or classify the TILs as either stromal TILs or epithelial TILs (see, e.g., fifth operation 110).

The method 100 comprises a sixth operation 112. At the sixth operation 112, one or more clusters of stromal TILs are generated. Each of the one or more clusters of stromal TILs comprises a subset of stromal TILs that are related to one another based on proximity. For example, based on the proximity of the stromal TILs in relation to one another, a first cluster of TILs and a second cluster of TILs may be generated. The first cluster of stromal TILs comprises a first subset of stromal TILs (e.g., a first collection of stromal TILs) and the second cluster of stromal TILs comprises a second subset of stromal TILs (e.g., a second collection of stromal TILs). In some embodiments, the stromal TILs of the first subset of stromal TILs do not comprise any of the stromal TILs of the second subset of stromal TILs, or vice versa. In other embodiments, some of the stromal TILs of the first subset of stromal TILs are also stromal TILs of the second subset of stromal TILs, or vice versa. In some embodiments, the one or more clusters of stromal TILs are generated via a graph theory technique. Generating the one or more clusters of stromal TILs includes acquiring electronic data, reading from a computer file, receiving a computer file, reading from a computer memory, or other computerized activity not practically performed in the human mind.

In some embodiments, the one or more clusters of stromal TILs may be generated by grouping the stromal TILs into corresponding clusters of the one or more clusters of stromal TILs based on a distance in which the stromal TILs are spaced from one another. In further embodiments, each stromal TIL of a given cluster of the one or more clusters of stromal TILs is spaced from a neighboring stromal TIL of the given cluster by less than a threshold distance. For example, the stromal TILs may comprise a first stromal TIL, a second stromal TIL, a third stromal TIL, a fourth stromal TIL, a fifth stromal TIL, and a sixth stromal TIL. The first, second, and third stromal TILs are grouped into a first cluster of stromal TILs, and the fourth, fifth, and sixth stromal TILs are grouped into a second cluster of stromal TILs. The first, second, and third stromal TILs are grouped into the first cluster of stromal TILs because each of the first, second, and third stromal TILs are spaced from at least one other of the first, second, and third stromal TILs by less than the threshold distance. The fourth, fifth, and sixth stromal TILs are grouped into the second cluster of stromal TILs because each of the fourth, fifth, and sixth stromal TILs are spaced from at least one other of the fourth, fifth, and sixth stromal TILs by less than the threshold distance. Further, first, second, and third stromal TILs are grouped into the first cluster of stromal TILs and the fourth, fifth, and sixth stromal TILs are grouped into the second cluster of stromal TILs because none of the first, second, or third stromal TILs are spaced from any of the fourth, fifth, or sixth stromal TILs by less than the threshold distance.

It will be appreciated that any number of clusters of TILs may be generated (e.g., 1 cluster, 2 clusters, 3 clusters, 20 clusters, 100 clusters, etc.). The number of clusters of stromal TILs is based on the proximity of the stromal TILs. For example, if any one of the first, second, or third stromal TILs were spaced from any of the fourth, fifth, or sixth stromal TILs by less than the threshold distance, the first, second, third, fourth, fifth, and sixth stromal TILs may be grouped into the first cluster of stromal TILs. On the other hand, it will be appreciated that if the first, second, third, fourth, fifth, and sixth stromal TILs were spaced differently—keeping in mind the threshold distance as described above—the first, second, third, fourth, fifth, and sixth stromal TILs may be grouped into three (or more) clusters of stromal TILs.

The method 100 comprises a seventh operation 114. At the seventh operation 114, a first plurality of architectural features are extracted from the digitized H&E slide image of the AA patient. The first plurality of architectural features are at least partially based on the cluster of stromal TILs. In other words, the first plurality of architectural features are architectural features of the TILs (ArcTILs) from the H&E slide of the AA patient.

The architectural features of the first plurality of architectural features are architectural features that have been determined to be (e.g., via a feature selection process, such as least absolute shrinkage and selection operator (LASSO), LASSO Cox regression, multivariable Cox regression model (MCRM), minimum redundancy maximum relevance (mRMR), best subsets selection, correlation feature selection, etc.) more relevant (e.g., discriminative) architectural features for predicting overall survival (OS) of AA patients with EC (e.g., the length of time from a given date that AA patients diagnosed with EC are still alive). Extracting the first plurality of architectural features includes acquiring electronic data, reading from a computer file, receiving a computer file, reading from a computer memory, or other computerized activity not practically performed in the human mind.

In some embodiments, each of the first plurality of architectural features corresponds to a different architectural feature of the one or more clusters of stromal TILs. For example, a first architectural feature of the first plurality of architectural features corresponds to a first architectural feature of the one or more clusters of stromal TILs, a second architectural feature of the first plurality of architectural features corresponds to a second architectural feature of the one or more clusters of stromal TILs that is different than the first architectural feature of the one or more clusters of stromal TILs, a third architectural feature of the first plurality of architectural features corresponds to a third architectural feature of the one or more clusters of stromal TILs that is different than both the first and second architectural features of the one or more clusters of stromal TILs, and so forth. In further embodiments, the first architectural feature may be a ratio of non-TILs (non-lymphocyte cells) density to a surrounding TIL one (e.g., a surrounding TIL density) in the epithelium (e.g., epithelial TILs and epithelial non-TILs). The second architectural feature may be the number of TIL clusters that are nearby (e.g., within a threshold distance) of a given non-TIL cluster in the epithelium. The third architectural feature may be the percentage of stromal non-TILs that are disposed within a twenty (20) micrometer proximity of a given non-TIL cluster.

In some embodiments, the first plurality of architectural features are based on the one or more clusters of stromal TILs. In further embodiments, the one or more clusters of stromal TILs may comprise only one cluster of stromal TILs and the first plurality of architectural features may be based only on the one cluster of stromal TILs. In some embodiments, the first plurality of architectural features may only be based on the one or more clusters of stromal TILs. In some embodiments, the first plurality of architectural features comprises at least four architectural features of the one or more clusters of stromal TILs. In some embodiments, the first plurality of architectural features consists of four architectural features of the one or more clusters of stromal TILs (e.g., the first plurality of architectural features includes only four architectural features of the one or more clusters of stromal TILs).

The method 100 comprises an eighth operation 116. At the eighth operation 116, a risk score is generated for the AA patient based on the first plurality of architectural features. In some embodiments, generating the risk score comprises assigning a value to each of the architectural features of the first plurality of architectural features. In other words, a plurality of values are assigned to the plurality of architectural features, respectively. In further embodiments, the values are based on the number of times a specific indicator (e.g., a difference in pixel intensity, pixel intensity within a predefined range, etc.) occurs in the digitized H&E slide of the AA patient. In yet further embodiments, the values are based on the number of times a specific indicator (e.g., a difference in pixel intensity, pixel intensity within a predefined range, etc.) occurs in the one or more clusters of stromal TILs.

In some embodiments, the values are based on the number of times a corresponding architectural feature of the plurality of architectural features is present in the digitized H&E slide image of the AA patient. In further embodiments, the values are based on the number of times a corresponding architectural feature of the plurality of architectural features is present in the one or more clusters of stromal TILs.

For example, the first architectural feature may be present ten times in the one or more clusters of stromal TILs (or the digitized H&E slide image of the AA patient). Thus, for the digitized H&E slide image of the AA patient, a value of ten is assigned to the first architectural feature. The second architectural feature may be present twenty times in the one or more clusters of stromal TILs (or the digitized H&E slide image of the AA patient). Thus, for the digitized H&E slide image of the AA patient, a value of twenty is assigned to the second architectural feature. It will be appreciated that different values, which are still based on the number of times a corresponding architectural feature of the plurality of architectural features is present in the digitized H&E slide image of the AA patient (or the one or more clusters of stromal TILs), may be assigned to the first plurality of architectural features (e.g., the assigned values may be normalized). For example, even though the first architectural feature may be present ten times in the one or more clusters of stromal TILs and the second architectural feature may be present twenty times in the one or more clusters of stromal TILs, a value of two may be assigned to the second architectural feature and a value of one may be assigned to the first architectural feature for the digitized H&E slide image of the AA patient (e.g., two to one is equivalent to twenty to ten).

In some embodiments, generating the risk score may include weighting the architectural features based on corresponding coefficients (e.g., the values are multiplied by respective weighting coefficients). In other words, a weighting coefficient is assigned to each of the values. In other words, the weighting coefficients are attached to the values, respectively. In some embodiments, each value is multiplied by its respective weighting coefficient to generate a plurality of weighted values.

The weighting coefficients may be generated by the feature selection model. For example, in some embodiments, the weighting coefficients are generated by a LASSO technique (e.g., the weights are selected by a LASSO feature selection model). In some embodiments, the architectural features of the first plurality of architectural features are standardized. For example, in some embodiments, the architectural features of the first plurality of architectural features are first standardized to have a mean of zero and a standard deviation of one (relative to a training dataset/cohort) so that hazard ratio (HR) and feature weights (e.g., weighting coefficients) are comparable across the first plurality of architectural features.

The values (or weighted values) are then combined to generate the risk score for the AA patient. The values (or weighted values) are combined based on a function. The function may comprise combining the values (or weighted values) by, for example, addition, subtraction, multiplication, division, some other mathematical operator, or a combination of the foregoing. In some embodiments, the risk score is generated based on a linear combination of the values (or weighted values). In other words, the values (or weighted values) are combined linearly to generate the risk score for the AA patient.

The risk score may be a number (e.g., a numerical value) that is based on the combination of the values (or weighted values). The risk score is prognostic of the OS of the AA patient (e.g., the risk score is predictive of OS of the AA patient). In some embodiments, the risk score is generated by using a LASSO technique. Generating the risk score for the AA patient includes acquiring electronic data, reading from a computer file, receiving a computer file, reading from a computer memory, or other computerized activity not practically performed in the human mind.

The method 100 comprises a ninth operation 118. At the ninth operation 118, a risk group classification for the AA patient is generated. Generating the risk group classification comprises classifying the AA patient into either a high risk group or a low risk group based, at least partially, on the risk score. In some embodiments, the high risk group indicates the AA patient will die before a threshold date, and the low risk group indicates the AA patient will die after or on the threshold date. In other embodiments, the high risk group indicates the AA patient will die on or before the threshold date, and the low risk group indicates the AA patient will die after the threshold date. In some embodiments, the threshold date is a predefined time (e.g., days, months, etc.) from either the date the AA patient is diagnosed with EC or the date the AA patient starts a treatment plan for their EC to the date in which the AA patient dies. Generating the risk group classification for the AA includes acquiring electronic data, reading from a computer file, receiving a computer file, reading from a computer memory, or other computerized activity not practically performed in the human mind.

In other embodiments, the high risk group indicates a probability that the AA patient will die within a date range is greater than a threshold probability, and the low risk group indicates the probability that the AA patient will die within the date range is less than or equal to the threshold probability. In other embodiments, the high risk group indicates the probability that the AA patient will die within the date range is greater than or equal to the threshold probability, and the low risk group indicates the probability that the AA patient will die within the date range is less than the threshold probability. For example, if a given AA patient is classified into the high risk group, the given AA patient may be twice as likely to die with 12 months than if the given AA patient was classified into the low risk group. As another example, if a given AA patient is classified into the high risk group, the given AA patient may be five times as likely to die with 36 months than if the given AA patient was classified into the low risk group.

In some embodiments, the date range is a predefined range of months (e.g., 12 months, 36 months, etc.). The date range may begin with either the date (e.g., the day) the AA patient is diagnosed with EC or the date the AA patient starts a treatment plan for their EC. In some embodiments, the threshold probability is a predefined probability value. In other embodiments, the threshold probability may be a predefined range of probabilities. In such embodiments, the high risk group may indicate the probability that the AA patient will die within the date range is greater than (or greater than or equal to) a maximum probability of the range of probabilities, and the low risk group may indicate the probability that the AA patient will die within the date range is less than or equal to (or less than) the minimum probability of the range of probabilities.

In some embodiments, classifying the AA patient into either the high risk group or the low risk group comprises comparing the risk score of the AA patient to a threshold risk score value. For example, in some embodiments, if the risk score of the AA patient is greater than the threshold risk score value, the AA patient is classified into the high risk group. In further embodiments, if the risk score of the AA patient is less than or equal to the threshold risk score value, the AA patient is classified into the low risk group. In other embodiments, if the risk score of the AA patient is greater than or equal to the threshold risk score value, the AA patient is classified into the high risk group; and if the risk score of the AA patient is less than the threshold risk score value, the AA patient is classified into the low risk group. In yet other embodiments, if the risk score of the AA patient is greater than (or equal to) the threshold risk score value, the AA patient is classified into the low risk group; and if the risk score of the AA patient is less than or equal to (or less than) the threshold risk score value, the AA patient is classified into the high risk group.

In some embodiments, the threshold risk score value is the median threshold risk score value of a group of other AA patients (e.g., a training dataset). In further embodiments, the AA patient may be classified into either the high risk group or the low risk group by comparing the risk score of the AA patient to the threshold risk score value due to a statistical model indicating that the risk score is significantly associated with OS of AA patient's (e.g., a Cox regression model produced a statistically significant result that indicated the risk score of a AA patient corresponds to the OS of the AA patient).

The method 100 comprises a tenth operation 120. At the tenth operation 120, the risk group classification of the AA patient is displayed. The risk group classification may be displayed on, for example, a computer monitor, a smartphone display, a tablet display, or some other display device, or a combination of the foregoing. It will be appreciated that the risk group classification may be displayed in other mediums (e.g., the classification may be printed on paper) in addition to, or in lieu of, displaying the risk group classification on a display device.

In some embodiments, the risk group classification may be displayed along with displaying one or more of the first plurality of architectural features of the AA patient (e.g., the values (or weighted values)), the risk score of the AA patient, the digitized H&E slide of the AA patient, some other classification of the patient (e.g., response of the AA patient to a treatment plan for the AA patient's EC, classification of the EC of the patient as aggressive or non-aggressive, etc.), or a combination of the foregoing.

In some embodiments, displaying the risk group classification also includes controlling a personalized medicine system, a computer monitor, or other display, to display operating parameters or characteristics of a machine learning classifier, during at least one of training and testing of the machine learning classifier, or during clinical operation of the machine learning classifier. In some embodiments, displaying the risk group classification comprises selecting for the risk group classification to be displayed via a graphical control element (e.g., by clicking/tapping on an item in a drop-down list). Displaying the risk group classification includes acquiring electronic data, reading from a computer file, receiving a computer file, reading from a computer memory, or other computerized activity not practically performed in the human mind.

By displaying the risk group classification, a medical practitioner may be able to easily and timely (e.g., intuitively due to the single classification being displayed) determine the time in which the AA patient has to live. Accordingly, the medical practitioner may be able to accurately guide the EC treatment of the AA patient to achieve better treatment results (e.g., expedite alternative treatment options (e.g., adjuvant therapy), choose a less aggressive treatment plan to reduce negative side effects, etc.). Further, the medical practitioner may be able to provide better care to the AA patient (e.g., improve patient satisfaction and/or knowledge)

by being able to better predict life expectancy and provide this information to the AA patient.

Figure 2:
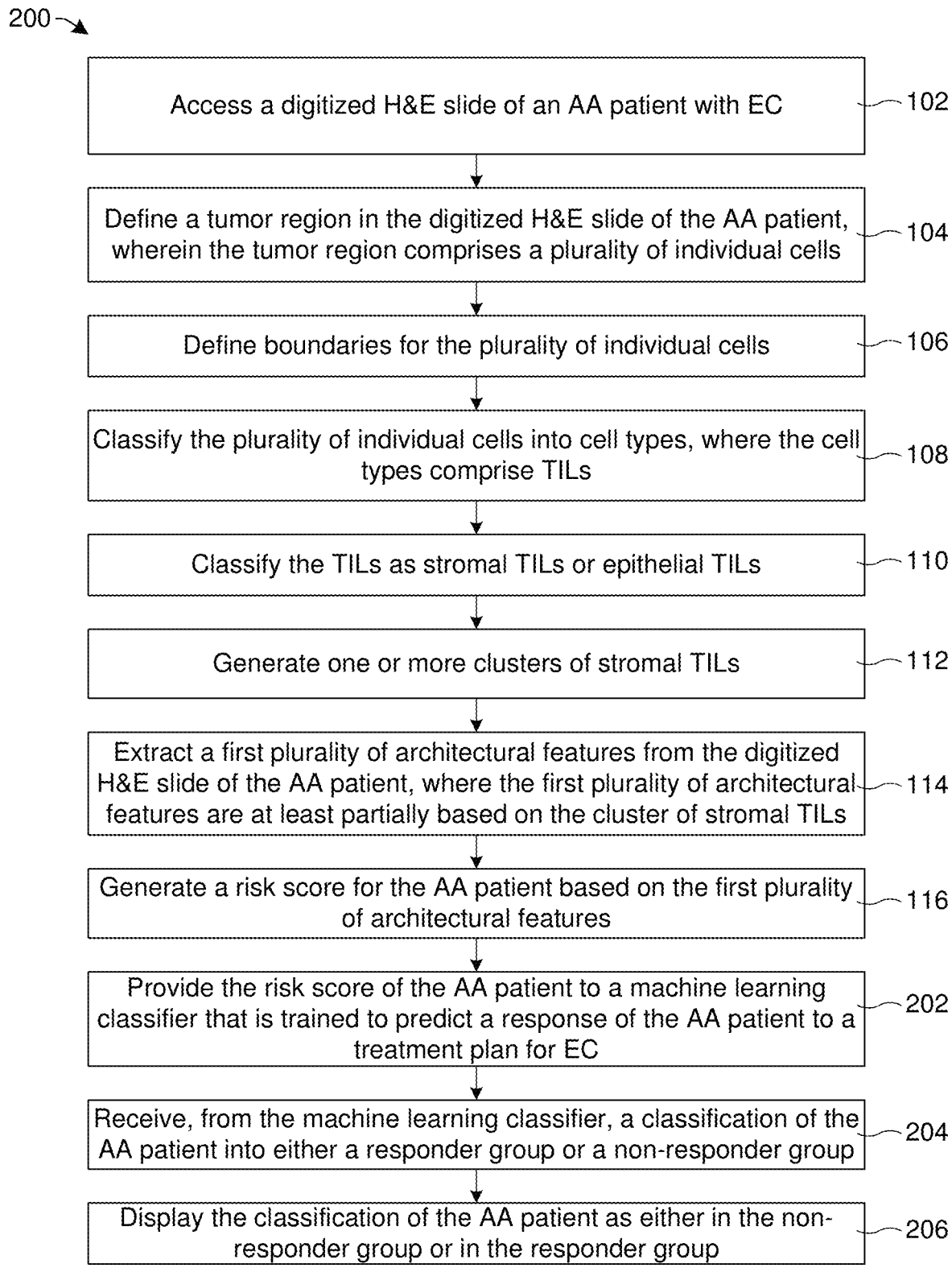
FIG. 2 illustrates some embodiments of a method for generating a prediction to a response to a treatment plan for EC for an AA patient with EC.

FIG. 2 illustrates some embodiments of a method 200 for generating a prediction to a response to a treatment plan for EC for an AA patient with EC. In some embodiments, the AA patient is referred to as a AA POI (e.g., due to the method 200 generating a prediction for the AA patient). The method 200 comprises operations 102-116 as described herein.

The method 200 comprises a first operation 202. At the first operation 202, the risk score is provided to a machine learning classifier. The machine learning classifier is trained to predict a response of the AA patient to a treatment plan for EC. The treatment plan comprises at least one of chemotherapy and radiotherapy. It will be appreciated that the treatment plan may comprise additional treatments, such as hormone therapy, targets therapy, biological therapy, or some other type of therapy. The machine learning classifier predicts the response of the AA patient to the treatment plan (e.g., chemoradiation) based on, at least in part, the risk score of the AA patient.

In some embodiments, the machine learning classifier may be, for example, a quadratic discriminant analysis (QDA) classifier, a support vector machine (SVM) classifier, a linear discriminant analysis (LDA) classifier, or some other machine learning classifier. Providing the risk score of the AA patient to the machine learning classifier includes acquiring electronic data, reading from a computer file, receiving a computer file, reading from a computer memory, or other computerized activity not practically performed in the human mind.

The method 200 comprises a second operation 204. At the second operation 204, a classification of the AA patient into either a responder group (RG) or a non-responder group (NRG) is received from the machine learning classifier. The RG indicates that the AA patient will respond to the treatment plan (e.g., the treatment plan will improve (e.g., eliminate, reduce, etc.) the EC of the AA patient. The NRG indicates that the AA patient will not respond to the treatment plan (e.g., the treatment plan will not improve the EC of the AA patient). The machine learning classifier classifies the AA patient into either the RG or the NRG based, at least in part, on the risk score of the AA patient (e.g., the machine learning classifier has been trained to predict a response to the treatment plan by classifying the AA patient into either the RG or the NRG based, at least in part, on the risk score of the AA patient). Receiving the classification of the AA patient as either in the NRG or in the RG includes acquiring electronic data, reading from a computer file, receiving a computer file, reading from a computer memory, or other computerized activity not practically performed in the human mind.

In some embodiments, the machine learning classifier classifies the AA patient into either the RG or the NRG by generating a classification value (e.g., a numerical value) based, at least in part, on the risk score of the AA patient. For example, in some embodiments, if the classification value (e.g., the numerical value) is less than (or greater than) a threshold classification value, the machine learning classifier classifies the AA patient into the NRG. On the other hand, if the classification value is greater than or equal to (or less than or equal to) the threshold classification value, the machine learning classifier classifies the AA patient into the RG. In other embodiments, if the classification value is less than or equal to (or greater than or equal to) the threshold classification value, the machine learning classifier classifies the AA patient into the NRG; and if the classification value is greater than (or less than) the threshold classification value, the machine learning classifier classifies the AA patient into the RG. It will be appreciated that other classification techniques may be employed.

The machine learning classifier classifies the AA patient into either the RG or the NRG based on the risk score of the AA patient (e.g., the machine learning classifier has been trained to predict a response to the treatment plan by classifying the AA patient into either the RG or the NRG based on the risk score of the AA patient). For example, the machine learning classifier generates the classification value based on the risk score of the patient.

In some embodiments, the machine learning classifier may classify the AA patient into either the RG or the NRG based on the risk score of the AA patient and at least one other feature that is prognostic of the OS of the AA patient (e.g., the machine learning classifier has been trained to predict a response to the treatment plan by classifying the AA patient into either the RG or the NRG based on both the risk score and the at least one other feature). For example, the machine learning classifier generates the classification value based on a combination of the risk score of the AA patient and the at least one other feature that is prognostic of the OS of the AA patient. The at least one other feature that is prognostic of the OS of the AA patient is different than the risk score. For example, the at least one other feature that is prognostic of the OS of the AA patient is a stage of the AA patient's EC. The stage of the AA patient's EC may be determined by a medical practitioner (e.g., chemotherapist) and/or by a processor configured to generate the AA patient's EC stage. The AA patient's EC stage may be generated before, after, or concurrently with generating the risk score of the AA patient.

The method 200 comprises a third operation 206. At the third operation 206, the classification of the AA patient as either in the NRG or in the RG is displayed.

The classification of the AA patient as either in the NRG or in the RG may be displayed on, for example, a computer monitor, a smartphone display, a tablet display, or some other display device, or a combination of the foregoing. It will be appreciated that the classification of the AA patient as either in the NRG or in the RG may be displayed in other mediums (e.g., the classification may be printed on paper) in addition to, or in lieu of, displaying the classification on a display device.

In some embodiments, the classification of the AA patient as either in the NRG or in the RG may be displayed along with displaying one or more of the first plurality of architectural features of the AA patient (e.g., the values (or weighted values)), the risk score of the AA patient, the H&E slide of the AA patient, some other classification of the patient (e.g., the risk group classification of the AA (see, e.g., tenth operation 120)), or a combination of the foregoing.

In some embodiments, displaying the classification of the AA patient as either in the NRG or in the RG also includes controlling a personalized medicine system, a computer monitor, or other display, to display operating parameters or characteristics of a machine learning classifier, during at least one of training and testing of the machine learning classifier, or during clinical operation of the machine learning classifier. In some embodiments, displaying the classification of the AA patient as either in the NRG or in the RG comprises selecting for the classification of the AA patient into either the NRG or the RG to be displayed via a graphical control element (e.g., by clicking/tapping on an item in a drop-down list). Displaying the classification of the AA patient as either in the NRG or in the RG includes acquiring electronic data, reading from a computer file, receiving a computer file, reading from a computer memory, or other computerized activity not practically performed in the human mind.

By displaying the classification of the AA patient as either in the NRG or in the RG, a medical practitioner may be able to easily and timely predict the AA patient's response to the treatment plan. Accordingly, the medical practitioner may be able to accurately guide the treatment of the AA patient to achieve better treatment results (e.g., maintain the treatment plan, change the treatment plan to expedite alternative treatment options, etc.).

Figure 3:
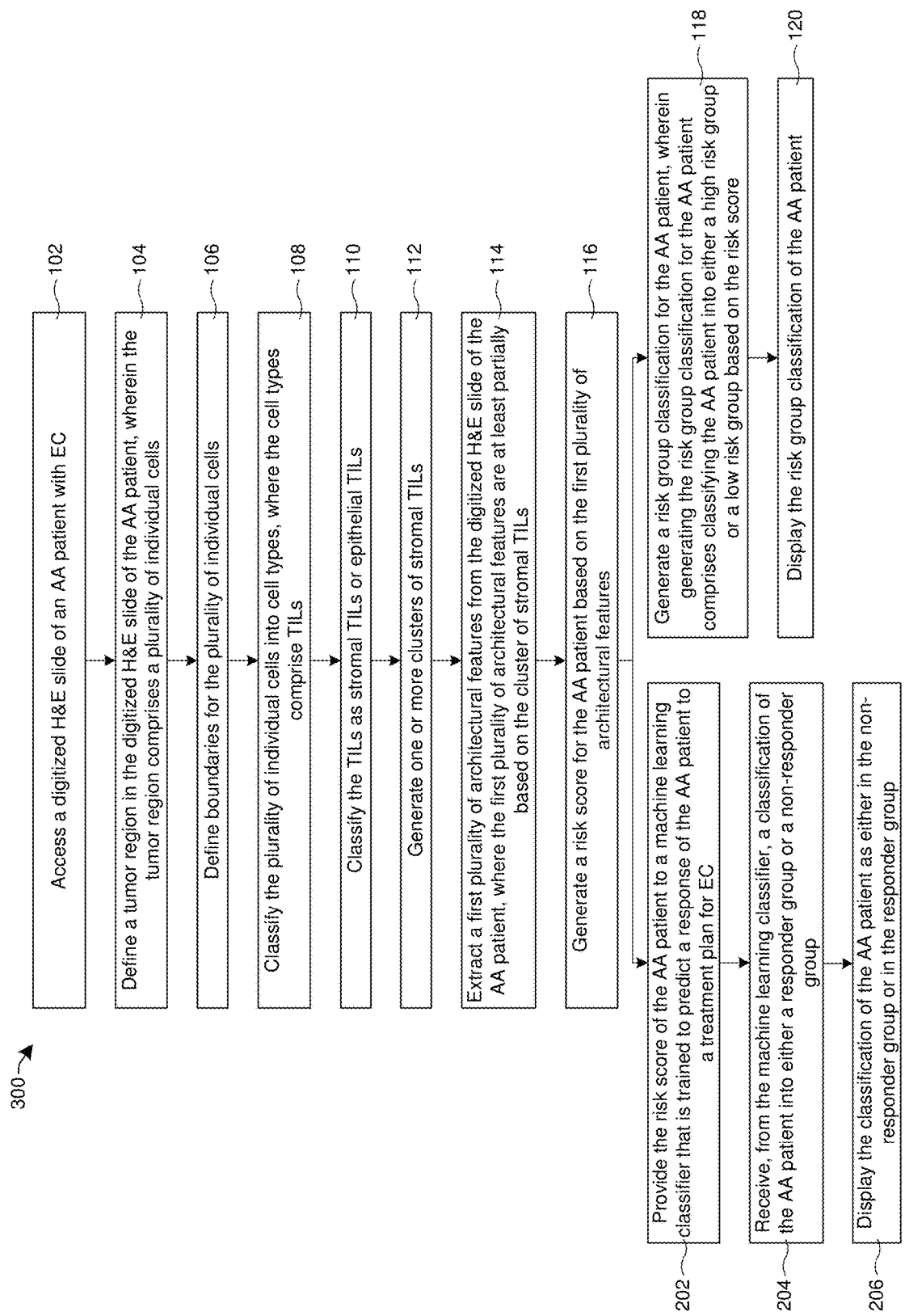
FIG. 3 illustrates some embodiments of a method for generating both a prediction for OS of an AA patient with EC and a prediction to a response to a treatment plan for EC for the AA patient with EC.

FIG. 3 illustrates some embodiments of a method 300 for generating both a prediction for OS of an AA patient with EC and a prediction to a response to a treatment plan for EC for the AA patient with EC. The method 300 comprises operations 102-116 and 202-206 as described herein.

As shown in the method 300 of FIG. 3, a risk score is generated for an AA patient based on a first plurality of architectural features (see, e.g., the eighth operation 116). A risk group classification for the AA patient is generated (see, e.g., the ninth operation 118). The risk group classification of the AA patient is displayed (see, e.g., the tenth operation 120). Further, the risk score of the AA patient is provided to a machine learning classifier that is trained to predict a response of the AA patient to a treatment plan for EC (see, e.g., the first operation 202). A classification of the AA patient into either a responder group or a non-responder group is received from the machine learning classifier (see, e.g., the second operation 204). The classification of the AA patient as either in the non-responder group or the responder group is displayed (see, e.g., the third operation 206).

In some embodiments, both the classification of the AA patient as either in the non-responder group or the responder group and the risk group classification of the AA patient are displayed. In other embodiments, at least one of the classification of the AA patient as either in the non-responder group or the responder group and the risk group classification of the AA patient is displayed.

Figure 4:
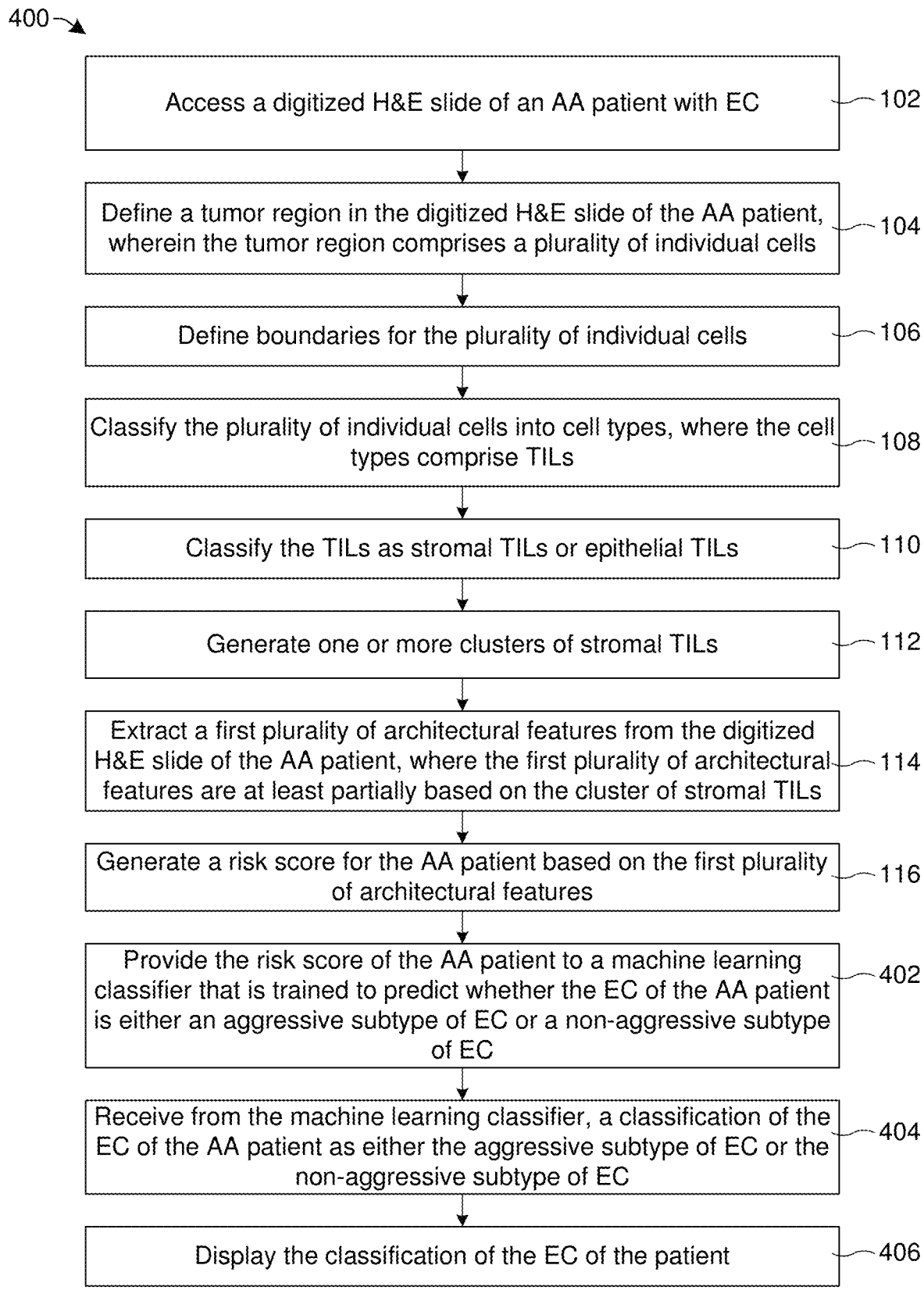
FIG. 4 illustrates some embodiments of a method for classifying an AA patient's EC as being an aggressive subtype of EC or a non-aggressive subtype of EC.

FIG. 4 illustrates some embodiments of a method 400 for classifying an AA patient's EC as being an aggressive subtype of EC or a non-aggressive subtype of EC. In some embodiments, the AA patient is referred to as a AA POI (e.g., due to the method 400 generating a prediction for the EC of the AA patient). The method 400 comprises operations 102-116 as described herein.

The method 400 comprises a first operation 402. At the first operation 402, the risk score is provided to a machine learning classifier. The machine learning classifier is trained to predict whether the EC of the AA patient is either an aggressive subtype of EC or a non-aggressive subtype of EC (also referred to as "predict(s) the EC subtype of the AA patient"). The machine learning classifier predicts the EC subtype of the AA patient based on, at least partially, the risk score of the AA patient. In some embodiments, the machine learning classifier is trained to predict a difference between an aggressive subtype of endometrial cancer (EC) and a non-aggressive subtype of EC. In such embodiments, the machine learning classifier may utilize the prediction of the difference between the aggressive subtype of EC and the non-aggressive subtype of EC to predict the EC subtype of the AA patient. In further such embodiments, training the machine learning classifier to predict the difference between the aggressive subtype of EC and the non-aggressive subtype of EC is based on architectural features corresponding to the first plurality of architectural features being extracted from other patients with EC (e.g., determining that the first plurality of architectural features are more predictive of correctly classifying the subtype of EC of AA patients of a training dataset than they are for classifying the subtype of EC of CA patients of the training dataset).

In some embodiments, the machine learning classifier may be, for example, a QDA classifier, a SVM classifier, a LDA classifier, or some other machine learning classifier. Providing the risk score of the AA patient to the machine learning classifier includes acquiring electronic data, reading from a computer file, receiving a computer file, reading from a computer memory, or other computerized activity not practically performed in the human mind.

The method 400 comprises a second operation 404. At the second operation 404, a classification of the EC of the AA patient as/into either the aggressive subtype of EC or the non-aggressive subtype of EC is received from the machine learning classifier. The machine learning classifier classifies the subtype of the EC of the AA patient based on the first plurality of architectural features of the AA patient.

In some embodiments, the machine learning classifier classifies the EC of the AA patient by generating a classification value (e.g., a numerical value) based, at least in part, on the risk score of the AA patient. It will be appreciated that other classification techniques may also be employed. Receiving the classification of the EC of the AA patient as either the aggressive subtype of EC or the non-aggressive subtype of EC includes acquiring electronic data, reading from a computer file, receiving a computer file, reading from a computer memory, or other computerized activity not practically performed in the human mind.

The method 400 comprises a third operation 406. At the third operation 406, the classification of the AA patient as either in the non-responder group or in the responder group is displayed. In other words, the classification of the AA patient's EC is displayed.

The classification of the AA patient's EC may be displayed on, for example, a computer monitor, a smartphone display, a tablet display, or some other display device, or a combination of the foregoing. It will be appreciated that the classification of the AA patient's EC may be displayed in other mediums (e.g., the classification may be printed on paper) in addition to, or in lieu of, displaying the classification on a display device.

In some embodiments, the classification of the AA patient's EC may be displayed along with displaying one or more of the first plurality of architectural features of the AA patient (e.g., the values (or weighted values)), the risk score of the AA patient, the H&E slide of the AA patient, one or more of other classifications of the patient (e.g., the risk group classification of the AA (see, e.g., tenth operation 120), the classification of the AA as either in a NRG or a RG (see, e.g., third operation 206)), or a combination of the foregoing.

In some embodiments, displaying the classification of the AA patient's EC also includes controlling a personalized medicine system, a computer monitor, or other display, to display operating parameters or characteristics of a machine learning classifier, during at least one of training and testing of the machine learning classifier, or during clinical operation of the machine learning classifier. In some embodiments, displaying the classification of the AA patient's EC comprises selecting for the classification of the AA patient's EC to be displayed via a graphical control element (e.g., by clicking/tapping on an item in a drop-down list). Displaying the classification of the AA patient's EC includes acquiring electronic data, reading from a computer file, receiving a computer file, reading from a computer memory, or other computerized activity not practically performed in the human mind.

By displaying the classification of the EC of the AA patient, a medical practitioner may be able to easily and timely predict the aggressiveness of the AA patient's EC. Accordingly, the medical practitioner may be able to accurately guide the treatment of the AA patient to achieve better treatment results.

Figure 5:
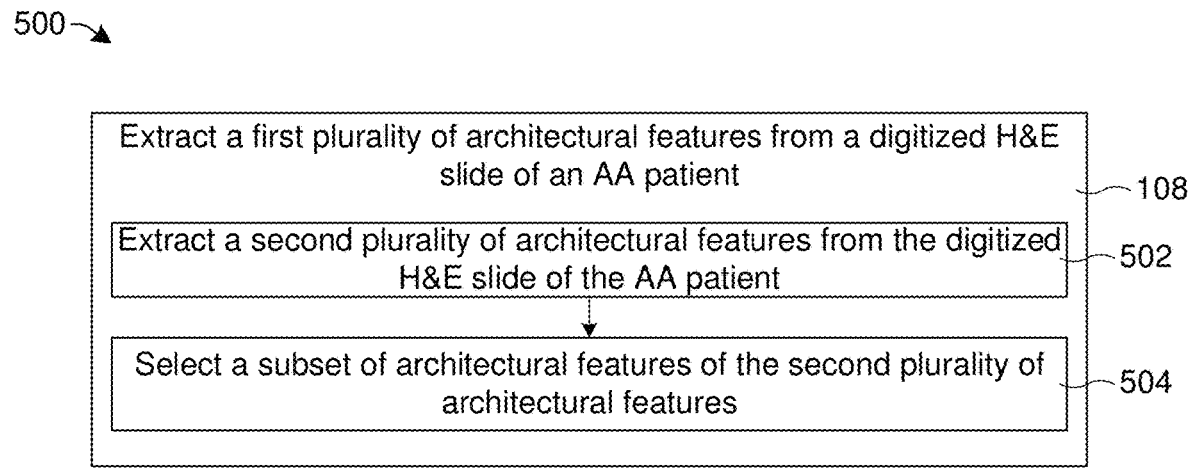
FIG. 5 illustrates a method of some more detailed embodiments of the seventh operation of the method of FIG. 1.

FIG. 5 illustrates a method 500 of some more detailed embodiments of the seventh operation 114 of the method 100 of FIG. 1. In other words, the method 500 illustrates some more detailed embodiments of extracting a first plurality of architectural features from the digitized H&E slide of the AA patient.

As shown in the method 500, in some embodiments, extracting the first plurality of architectural features from the digitized H&E slide of the AA patient comprises a first operation 502. At the first operation 502, a second plurality of architectural features are extracted from the digitized H&E slide of the AA patient. Extracting the second plurality of architectural features includes acquiring electronic data, reading from a computer file, receiving a computer file, reading from a computer memory, or other computerized activity not practically performed in the human mind.

At least some of the architectural features of the second plurality of architectural features are extracted from the tumor region of the digitized H&E slide of the AA patient. At least some of the architectural features of the second plurality of architectural features are extracted from the one or more clusters of stromal TILs. At least some of the architectural features of the second plurality of architectural features may be extracted from one or more clusters of epithelial TILs (e.g., substantially similar to (and substantially similarly generated as) the one or more clusters of stromal TILs). At least some of the architectural features of the second plurality of architectural features may be extracted from the TILs of the plurality of individual cells. At least some of the architectural features of the second plurality of architectural features may be extracted from the non-lymphocyte cells (e.g., stromal non-lymphocyte cells) of the plurality of individual cells. At least some of the architectural features of the second plurality of architectural features may be extracted from the cancer cells of the plurality of individual cells.

The method 500 further comprises a second operation 504. At the second operation 504, a subset of architectural features of the second plurality of architectural features are selected. The subset of architectural features define the first plurality of architectural features. In other words, the first plurality of architectural features consist of the subset of architectural features of the second plurality of architectural features.

The subset of architectural features are selected from the second plurality of architectural features by determining which architectural features of the second plurality of architectural features are more relevant (e.g., the most discriminative) for predicting overall survival (OS) of AA patients with EC. A feature selection process determines which architectural features of the second plurality of architectural features are more relevant (e.g., discriminative) for predicting OS of AA patients with EC. The architectural features of the second plurality of architectural features that are found (e.g., via the feature selection process) to be more relevant (e.g., the most discriminative) for predicting OS of AA patients with EC are selected as the subset of architectural features.

In some embodiments, the feature selection process may be, for example, LASSO, LASSO Cox regression, multivariable Cox regression model (MCRM), mRMR, best subsets selection, correlation feature selection, or the like. In further embodiments, the feature selection is LASSO Cox regression. In embodiments in which the feature selection is LASSO Cox regression, the subset of architectural features may be more relevant than another, different subset of architectural features of the second plurality of architectural features which were selected by a different feature selection process (e.g., mMRM). Selecting the subset of architectural features includes acquiring electronic data, reading from a computer file, receiving a computer file, reading from a computer memory, or other computerized activity not practically performed in the human mind.

Figure 6:
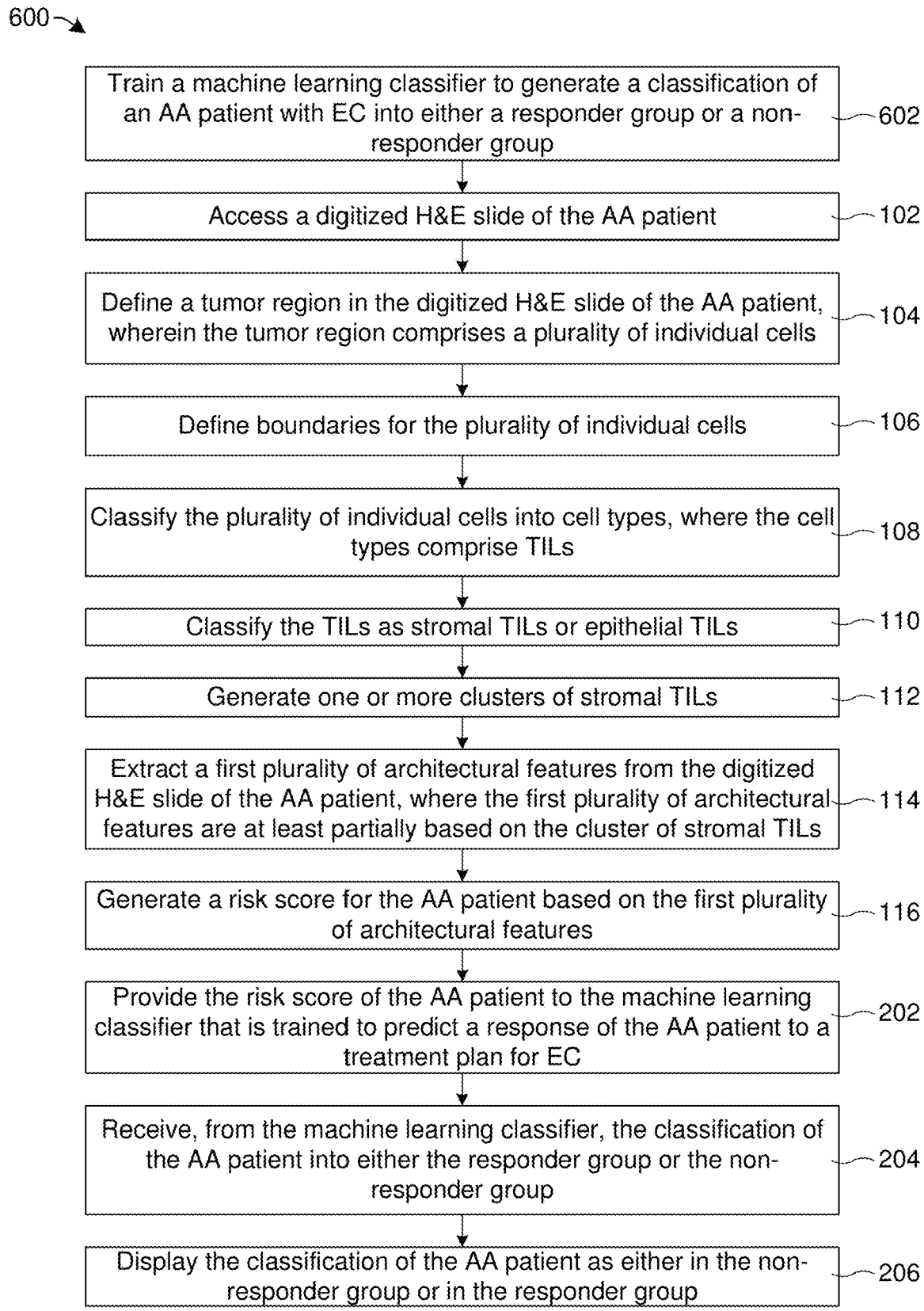
FIG. 6 illustrates a method of some other embodiments of the method of FIG. 2.

FIG. 6 illustrates a method 600 of some other embodiments of the method of FIG. 2. The method 600 is similar to the method 200 of FIG. 2 and includes operations 102-116 and 202-206, but also includes a first operation 602. At the first operation 602, a machine learning classifier is trained to generate a classification of an AA patient with EC into either a responder group or a non-responder group (e.g., the RG and NRG described in reference to method 200). In some embodiments, the AA patient is referred to as an AA POI (e.g., due to the method 600 generating a prediction for the AA patient).

While not shown explicitly in figures, it will be appreciated that the method 100 of FIG. 1, the method 300 of FIG. 3, and the method 400 of FIG. 4 may also comprise a corresponding operation of training a machine learning classifier. For example, the method 100 of FIG. 1 may comprise an operation of training a machine learning classifier to generate a risk group classification (e.g., the risk group classification described in reference to method 100). In some embodiments, the method 300 of FIG. 3 may comprise an operation of training a machine learning classifier to generate a risk group classification (e.g., the risk group classification described in reference to method 100) and training the machine learning classifier to generate a classification of an AA patient with EC into either a responder group or a non-responder group. In some embodiments, the method 400 of FIG. 4 may comprise an operation of training a machine learning classifier to predict whether the EC of the AA patient is either an aggressive subtype of EC or a non-aggressive subtype of EC (e.g., the aggressive subtype of EC or the non-aggressive subtype of EC described in reference to method 400).

Figure 7:
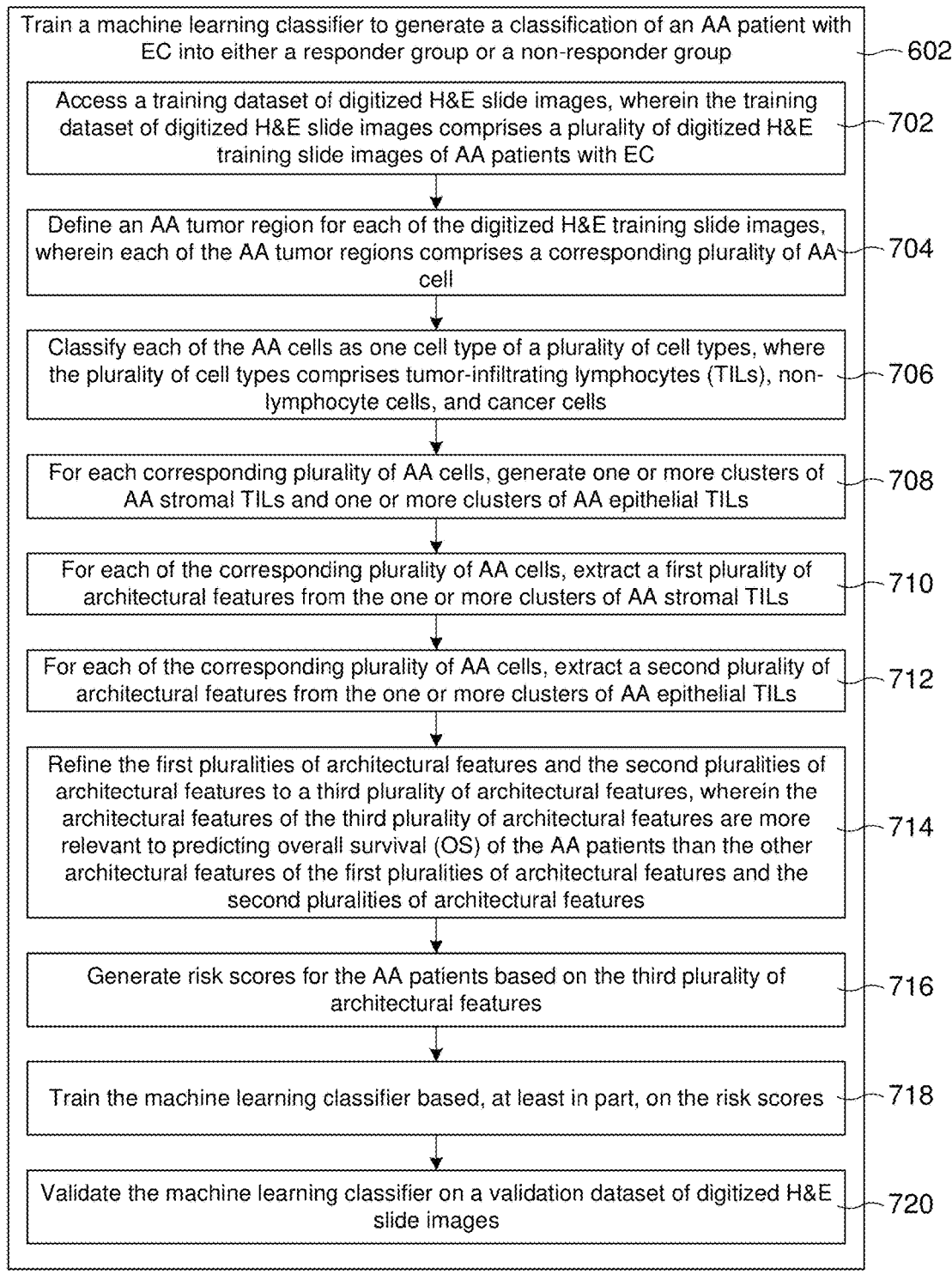
FIG. 7 illustrates a method of some embodiments of the first operation of the method of FIG. 6.

FIG. 7 illustrates a method 700 of some embodiments of the first operation 602 of the method 600 of FIG. 6. In other words, the method 700 illustrates some embodiments of training a machine learning classifier to generate a classification of an AA patient with EC (also known as a AA POI) into either a responder group or a non-responder group.

The method 700 comprises a first operation 702. At the first operation 702, a training dataset of digitized H&E slide images is accessed. The training dataset comprises a plurality of digitized H&E training slide images (e.g., data from a plurality of digitized H&E training slide images). Each of the plurality of digitized H&E training slide images demonstrates tissue from a uterus of a corresponding AA patient and a portion of a gynecologic tumor of the corresponding AA patient. Further, each of the plurality of digitized H&E training slide images is associated with a past AA patient that has EC.

For example, the plurality of digitized H&E training slide images comprises a first digitized H&E training slide image, a second digitized H&E training slide image, and so forth.

The first digitized H&E training slide image is associated with a first past AA patient with EC (e.g., a first AA woman who was diagnosed with EC at an earlier time), the second digitized H&E training slide image is associated with a second past AA patient with EC (e.g., a second (different) AA woman who was diagnosed with EC at an earlier time), and so forth. Accessing the training dataset includes acquiring electronic data, reading from a computer file, receiving a computer file, reading from a computer memory, or other computerized activity not practically performed in the human mind.

The method 700 comprises a second operation 704. At the second operation 704, a tumor region (also referred to as AA tumor region) in each of the digitized H&E slides of the AA patients is defined. Each tumor region comprises a plurality of individual cells of a corresponding one of the AA patients. For example, the tumor region of the first digitized H&E training slide image comprises a plurality of individual cells of the first past AA patient, the tumor region of the second digitized H&E training slide image comprises a plurality of individual cells of the second past AA patient, and so forth. In some embodiments, the plurality of individual cells of the past AA patients are referred to as the plurality of AA cells. For example, the plurality of individual cells of the first past AA patient may be referred to as a (first) plurality of AA cells, the plurality of individual cells of the second past AA patient may be referred to as a (second) plurality of AA cells, and so forth. In further embodiments, the plurality of individual cells of the past AA patients (the plurality of AA cells of the past AA patients) may be collectively referred to as the pluralities of individual cells of the past AA patients (the pluralities of AA cells of the past AA patients).

The second operation 704 is substantially similar (e.g., having the same general process) to the second operation 104, except the second operation 704 defines a tumor region for each of the digitized H&E slides of the AA patients (each of the plurality of digitized H&E training slide images), whereas the second operation 104 defines a tumor region for a digitized H&E slide image of an AA patient with EC (also referred to as "a digitized H&E slide image of an AA POI").

The method comprises 700 a third operation 706. At the third operation 706, each of the AA cells are classified as one cell type of a plurality of cell types. The plurality of cell types comprises tumor-infiltrating lymphocytes (TILs), non-lymphocyte cells, and cancer cells. The third operation 706 is substantially similar to the fourth operation 108, except the third operation 706 classifies each of the AA cells of each of the plurality of AA cells of the past AA patients to a specific cell type, whereas the fourth operation 108 classifies the plurality of individual cell of the patient with EC (also referred to as "the plurality of AA cells of the AA POI").

The method 700 comprises a fourth operation 708. At the fourth operation 708, for each of the corresponding plurality of AA cells, one or more clusters of AA stromal TILs and one or more clusters of AA epithelial TILs are generated. For example, one or more clusters of AA stromal TILs and one or more clusters of AA epithelial TILs are generated for the plurality of AA cells of the first past AA patient, one or more clusters of AA stromal TILs and one or more clusters of AA epithelial TILs are generated for the plurality of AA cells of the second past AA patient, and so forth.

The fourth operation 708 is substantially similar to the sixth operation 112, except the fourth operation 708 generates one or more clusters of AA stromal TILs and one or more clusters of AA epithelial TILs for each of the pluralities of AA cells, whereas the sixth operation 112 generates one or more clusters of AA stromal TILs (and generating one or more clusters of AA epithelial TILs in a similar manner as the one or more clusters of AA stromal TILs are generated, for example, based on proximity) for the plurality of individual cell of the patient with EC (also referred to as "the plurality of AA cells of the AA POI").

In some embodiments, the method 700 may also comprises defining a boundary for each of the AA cells of each of the corresponding pluralities of AA cells (see, e.g., third operation 106 of the method 100 of FIG. 1). In such embodiments, the clusters of the one or more clusters of stromal TILs, one or more clusters of stromal non-lymphocyte cell, one or more clusters of epithelial TILs, one or more clusters of cancer cells, and the like, may be based on grouping cells of the same type (e.g., stromal TILs) based on proximity. In further such embodiments, the proximity of cells may be based on a distance in which boundaries of neighboring cells of the same type are spaced from one another (e.g., less than or greater than a threshold distance).

The method comprises 700 a fifth operation 710. At the fifth operation 710, for each of the corresponding plurality of AA cells, a first plurality of architectural features are extracted from the one or more clusters of AA stromal TILs. In other words, for each of the corresponding plurality of AA cells, a first plurality of architectural features are extracted from the digitized H&E training slide images, where the first plurality of architectural features are at least partially based on corresponding ones of the one or more clusters of stromal TILs. For example, a first plurality of architectural features are extracted from the one or more clusters of stromal TILs that were generated for the first past AA patient, a first plurality of architectural features are extracted from the one or more clusters of stromal TILs that were generated for the second past AA patient, and so forth.

In some embodiments, the first plurality of architectural features are collectively referred to as (e.g., each of the first plurality of architectural features are collectively referred to as) first pluralities of architectural features. For example, the first pluralities of architectural features comprise the first plurality of architectural features that were extracted from the one or more clusters of stromal TILs that were generated for the first past AA patient, the first plurality of architectural features that were extracted from the one or more clusters of stromal TILs that were generated for the second past AA patient, and so forth.

The fifth operation 710 is substantially similar to the seventh operation 114, except the fifth operation 710 comprises extracting a first plurality of architectural features from the one or more clusters of AA stromal TILs for each of the corresponding plurality of AA cells, whereas the seventh operation 114 extracts a first plurality of architectural features from the digitized H&E slide image of the AA patient (also referred to as "the digitized H&E slide image of the AA POI").

The method comprises 700 a sixth operation 712. At the sixth operation 712, for each of the corresponding plurality of AA cells, a second plurality of architectural features are extracted from the one or more clusters of AA epithelial TILs. In other words, for each of the corresponding plurality of AA cells, a second plurality of architectural features are extracted from the digitized H&E training slide images, where the second plurality of architectural features are at least partially based on corresponding ones of the one or more clusters of epithelial TILs. For example, a second plurality of architectural features are extracted from the one or more clusters of epithelial TILs that were generated for the first past AA patient, a second plurality of architectural features are extracted from the one or more clusters of epithelial TILs that were generated for the second past AA patient, and so forth.

In some embodiments, the second plurality of architectural features are collectively referred to as (e.g., each of the second plurality of architectural features are collectively referred to as) second pluralities of architectural features. For example, the second pluralities of architectural features comprise the second plurality of architectural features that were extracted from the one or more clusters of epithelial TILs that were generated for the first past AA patient, the second plurality of architectural features that were extracted from the one or more clusters of epithelial TILs that were generated for the second past AA patient, and so forth.

The sixth operation 712 is substantially similar to the fifth operation 710, except the sixth operation 712 extracts a second plurality of architectural features from the one or more clusters of AA epithelial TILs for each of the corresponding plurality of AA cells, whereas the fifth operation 710 extracts a first plurality of architectural features from the one or more clusters of AA stromal TILs for each of the corresponding plurality of AA cells.

The method comprises 700 a seventh operation 714. At the seventh operation 714, the first pluralities of architectural features and the second pluralities of architectural features are refined to a third plurality of architectural features. The architectural features of the third plurality of architectural features are more relevant to predicting OS of the AA patients than the other architectural features of the first pluralities of architectural features and the second pluralities of architectural features.

For example, each of the first pluralities of architectural features may comprise 40 different architectural features that were extracted from the one or more clusters of AA stromal TILs of a corresponding AA patient (e.g., a corresponding AA patient from the training cohort). Likewise, each of the second pluralities of architectural features may comprise 45 different architectural features that were extracted from the one or more clusters of AA epithelial TILs of a corresponding AA patient (e.g., a corresponding AA patient from the training cohort). In other words, for each of the AA patients with EC (training cohort AA patients), 85 different architectural features may be extracted from each of the digitized H&E training slide images (e.g., 40 different architectural features from clusters of stromal TILs and 45 different architectural features from clusters of epithelial TILs). The architectural features of the third plurality of architectural features are more relevant (e.g., more discriminative) of the AA patients than the other architectural features of the first pluralities of architectural features and the second pluralities of architectural features A feature selection process determines which architectural features of the AA patients are more relevant to OS of the AA patients than the other architectural features of the first pluralities of architectural features and the second pluralities of architectural features. In some embodiments, the feature selection process may be, for example, LASSO, LASSO Cox regression, MCRM mRMR, best subsets selection, correlation feature selection, or the like. In further embodiments, the feature selection is MCRM. In embodiments in which the feature selection is MCRM, the third plurality of architectural features may be more relevant than another, different refined plurality of architectural features of the second and third pluralities of architectural features which were selected by a different feature selection process (e.g., best subsets). In further embodiments, refining the first pluralities of architectural features and the second pluralities of architectural features to the third plurality of architectural features includes acquiring electronic data, reading from a computer file, receiving a computer file, reading from a computer memory, or other computerized activity not practically performed in the human mind.

In some embodiments, the third plurality of architectural features comprises architectural features from only the first plurality of architectural features. In other words, each of the architectural features of the third plurality of architectural features corresponds to only one of the architectural features of the first plurality of architectural features. More specifically, each of the architectural features of the third plurality of architectural features corresponds to an architectural feature that was extracted from the one or more clusters of AA stromal TILs. For example, the first plurality of architectural features is extracted from each of the past AA patients. Each of the architectural features of the first plurality of architectural features are based on the one or more clusters of stromal TILs of a corresponding past AA patient. The architectural features of the third plurality of architectural features may only comprise architectural features of the first plurality of architectural features and not any architectural features of the second plurality of architectural features, which also were extracted from each of the past AA patients.

The method 700 comprises an eighth operation 716. At the eighth operation 716, risk scores are generated for the AA patients, respectively. For example, a first risk score is generated for the first past AA patient, a second risk score is generated for the second past AA patient, and so forth. Each of the risk scores is generated based on a corresponding third plurality of architectural features. For example, the first risk score is generated based on the third plurality of architectural features that were extracted from the digitized H&E training slide image of the first past AA patient (e.g., extracted because the third plurality of architectural features are architectural features from either the first or second pluralities of architectural features), the second risk score is generated based on the third plurality of architectural features that were extracted from the digitized H&E training slide image of the second past AA patient, and so forth. Each of the risk scores is prognostic of OS of a corresponding past AA patient. For example, the first risk score is prognostic of the OS of the first past AA patient, the second risk score is prognostic of the OS of the second past AA patient, and so forth.

The eighth operation 716 is substantially similar to the eighth operation 116, except the eighth operation 716 generates a risk score for each of the past AA patients, whereas the eighth operation 116 generates a risk score for the AA patient (also referred to as "the AA POI").

The method 700 comprises a ninth operation 718. At the ninth operation 718, the machine learning classifier is trained based, at least in part, on the risk scores of the AA patients. In some embodiments, the machine learning classifier is trained to generate a classification of the AA patient (the AA POI) into either a responder group or a non-responder group (see, e.g., the method 200 of FIG. 2). In some embodiments, the machine learning classifier is trained to predict whether the EC of the AA patient (the EC of the AA POI) is either an aggressive subtype of EC or a non-aggressive subtype of EC (see, e.g., the method 400 of FIG. 4). In such embodiments, the first operation 602 comprises training a machine learning classifier to predict whether the EC of the AA patient (the EC of the AA POI) is either an aggressive subtype of EC or a non-aggressive subtype of EC. In some embodiments, the machine learning classifier may be trained to generate a risk group classification of the AA patient (the AA POI) (see, e.g., the method 100 of FIG. 1). In such embodiments, the first operation 602 comprises training a machine learning classifier to generate a risk group classification of the AA patient (the AA POI).

In some embodiments, the machine learning classifiers may be, for example, a QDA classifier, a SVM classifier, a LDA classifier, or some other machine learning classifier. In further embodiments, the machine learning classifier may be trained based on, at least in part, the risk scores and at least one other feature that is prognostic of the OS (e.g., stage of past AA patient's EC). Training the machine learning classifier includes acquiring electronic data, reading from a computer file, receiving a computer file, reading from a computer memory, or other computerized activity not practically performed in the human mind.

The method 700 comprises a tenth operation 720. At the tenth operation 720, the machine learning classifier is validated on a validation dataset of digitized H&E slide images. The validation dataset comprises a plurality of digitized H&E validation slide images. Each of the plurality of digitized H&E validation slide images demonstrates tissue from a uterus of a corresponding AA patient and a portion of a gynecologic tumor of the corresponding AA patient. Further, each of the plurality of digitized H&E validation slide images is associated with a past AA patient that has EC.

Further, the validation dataset and the training dataset are portions of an original dataset (e.g., a larger collection of digitized H&E slide images). The original dataset comprises a plurality of original digitized H&E slide images. Each of the plurality of original digitized H&E slide images demonstrates tissue from a uterus of a corresponding AA patient and a portion of a gynecologic tumor of the corresponding AA patient. Further, each of the plurality of original digitized H&E slide images is associated with a past AA patient that has EC. The original dataset is partitioned into the validation dataset and the training dataset. In some embodiments, the original dataset is partitioned into the validation dataset and the training dataset by randomly placing the original digitized H&E slide images into either the validation dataset or the training dataset.

The machine learning classifier is validated on the validation dataset. In some embodiments, the machine learning classifier is validated on the validation dataset to ensure that the machine learning classifier is adequately able to predict a response of the AA patient (the AA POI) to a treatment plan for EC (e.g., generate a classification of the AA patient (AA POI) into either the responder group or non-responder group). In some embodiments, the machine learning classifier is validated on the validation dataset to ensure that the machine learning classifier is adequately able to predict whether the EC of the AA patient (the EC of the AA POI) is either an aggressive subtype of EC or a non-aggressive subtype of EC. In some embodiments, the machine learning classifier is validated on the validation dataset to ensure that the machine learning classifier is adequately able to generate a risk group classification of the AA patient (the AA POI). In some embodiments, a k-fold cross-validation is utilized to validate the machine learning classifier. In further embodiments, a 10-fold cross-validation is utilized to validate the machine learning classifier. It will be appreciated that, in other embodiments, other cross-validation techniques may be utilized to validate the machine learning classifier.

Figure 8:
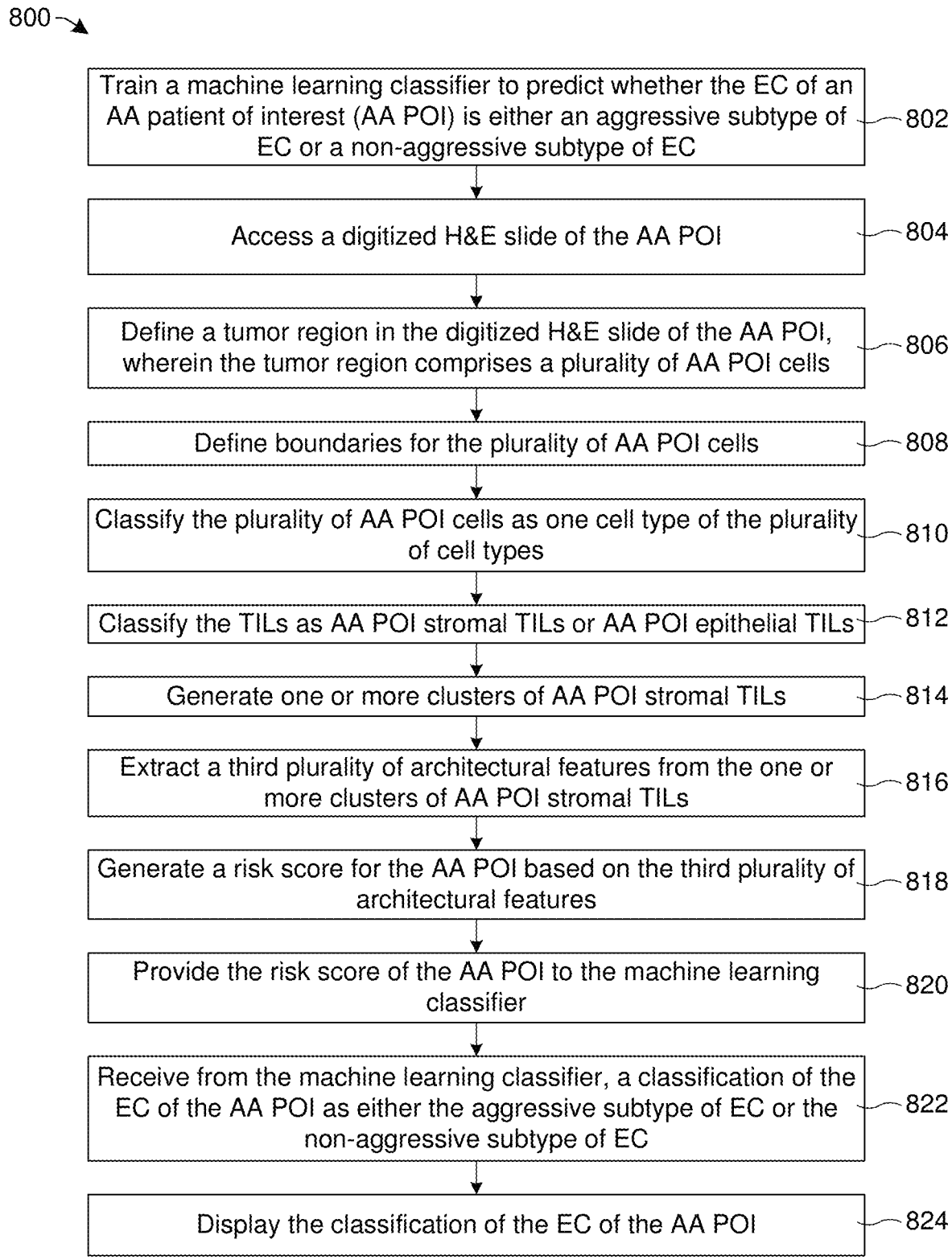
FIG. 8 illustrates some embodiments of a method for classifying whether the EC of an AA POI is either an aggressive subtype of EC or a non-aggressive subtype of EC.

FIG. 8 illustrates some embodiments of a method 800 for classifying whether the EC of an AA POI is either an aggressive subtype of EC or a non-aggressive subtype of EC.

The method 800 comprises a first operation 802. At the first operation 802, a machine learning classifier is trained to predict whether the EC of an AA POI is either an aggressive subtype of EC or a non-aggressive subtype of EC. The first operation 802 may be substantially the same (e.g., comprise substantially similar steps/processes, items, features, etc.) as the first operation 602 described herein.

The method 800 comprises a second operation 804. At the second operation 804, a digitized H&E slide image of the AA POI is accessed. The digitized H&E slide image of the AA POI indicates the AA POI has EC. The digitized H&E slide image of the AA POI demonstrates tissue from a uterus of the AA POI and at least a portion of a gynecologic tumor. The second operation 804 may be substantially the same as the first operation 102 described herein.

The method 800 comprises a third operation 806. At the third operation 806, a tumor region is defined in the digitized H&E slide image of the AA POI. The tumor region comprises a plurality of AA POI cells. The third operation 806 may be substantially the same as the second operation 104 described herein.

The method 800 comprises a fourth operation 808. At the fourth operation 808, a boundary for each of the plurality of AA POI cells is defined. The fourth operation 808 may be substantially the same as the third operation 106 described herein.

The method 800 comprises a fifth operation 810. At the fifth operation 810, each of the plurality of AA POI cells are classified as one cell type of the plurality of cell types. In some embodiments, the plurality of cell types is the same plurality of cell types utilized in the first operation 802 (see, e.g., the third operation 706 of the method 700 of FIG. 7). The fifth operation 810 may be substantially the same as the third operation 706 described herein.

The method 800 comprises a sixth operation 812. At the sixth operation 812, the TILs of the AA POI as classified as either AA POI stromal TILs or AA POI epithelial TILs. The sixth operation 812 may be substantially the same as the fifth operation 110 described herein.

The method 800 comprises a seventh operation 814. At the seventh operation 814, one or more clusters of AA POI stromal TILs are generated. The seventh operation 814 may be substantially the same as the sixth operation 112 described herein.

The method 800 comprises an eighth operation 816. At the eighth operation 816, a third plurality of architectural features are extracted from the one or more clusters of AA POI stromal TILs. In some embodiments, the third plurality of architectural features is the same third plurality of architectural features utilized in the first operation 802 (see, e.g., the seventh operation 714 of the method 700 of FIG. 7). The eighth operation 816 may be substantially the same as the seventh operation 114 described herein.

The method 800 comprises a ninth operation 818. At the ninth operation 818, a risk score for the AA POI is generated based on the third plurality of architectural features. The ninth operation 818 may be substantially the same as the eighth operation 116 described herein.

The method 800 comprises a tenth operation 820. At the tenth operation 820, the risk score for the AA POI is provided to the machine learning classifier. The tenth operation 820 may be substantially the same as the first operation 402 described herein.

The method 800 comprises an eleventh operation 822. At the eleventh operation 822, a classification of the EC of the AA POI into either the aggressive subtype of EC or the non-aggressive subtype of EC is received from the machine learning classifier. The eleventh operation 822 may be substantially the same as the second operation 404 described herein.

The method 800 comprises a twelfth operation 824. At the twelfth operation 824, the classification of the EC of the AA POI is displayed. The twelfth operation 824 may be substantially the same as the third operation 406 described herein.

Figure 9:
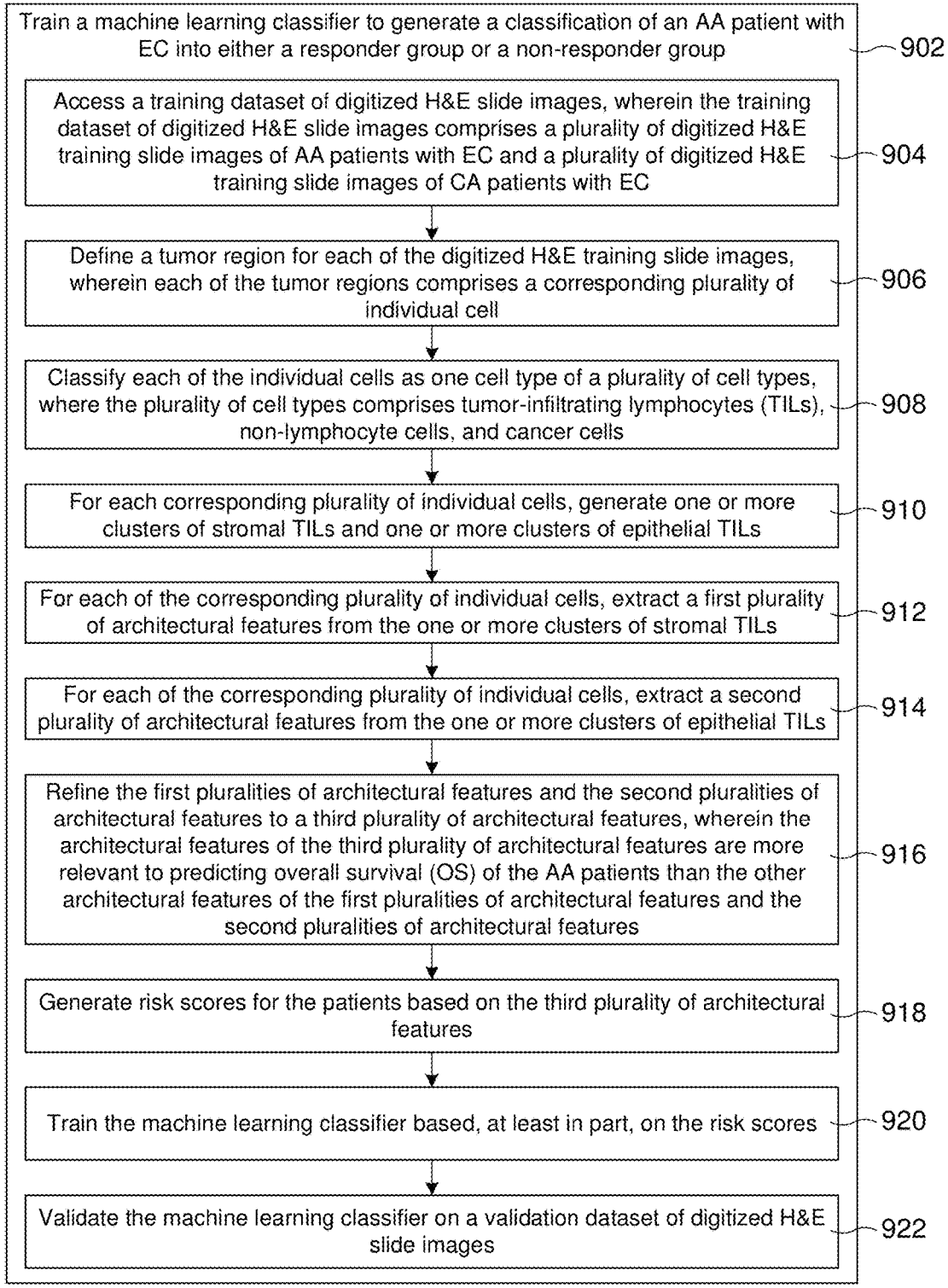
FIG. 9 illustrates a method of some other embodiments of the method of FIG. 7.

FIG. 9 illustrates a method 900 of some other embodiments of the method of FIG. 7.

The method 900 comprises a first operation 902. At the first operation 902, a machine learning classifier is trained to generate a classification of an AA patient (an AA POI) with EC into either a responder group or a non-responder group. The first operation 902 may be substantially the same (e.g., comprise substantially similar steps/processes, items, features, etc.) as the first operation 602 described herein. The first operation comprises a second operation 904, a third operation 906, a fourth operation 908, a fifth operation 910, a sixth operation 912, a seventh operation 914, an eighth operation 916, a ninth operation 918, a tenth operation 920, and an eleventh operation 922.

At the second operation 904, a training dataset of digitized H&E slide images is accessed. The training dataset comprises a plurality of digitized H&E training slide images that correspond to AA patients with EC and a plurality of digitized H&E training slide images that correspond to Caucasian American (CA) patients with EC. For example, the plurality of digitized H&E training slide images comprises a first digitized H&E training slide image corresponding to a first past AA patient, a second digitized H&E training slide image corresponding to a second past AA patient, a third digitized H&E training slide image corresponding to a first past CA patient, a fourth digitized H&E training slide image corresponding to a second past CA patient, and so forth.

Each of the plurality of digitized H&E training slide images demonstrates tissue from a uterus of a corresponding patient and a portion of a gynecologic tumor of the corresponding patient. Further, each of the plurality of digitized H&E training slide images is associated with a past patient that has EC. The second operation 904 may be substantially the same (e.g., comprise substantially similar steps/processes, items, features, etc.) as the first operation 702 described herein.

At the third operation 906, a tumor region in each of the digitized H&E slides is defined. Each tumor region comprises a plurality of individual cells of a corresponding past patient with EC. For example, the tumor region of the first digitized H&E training slide image comprises a plurality of individual cells of the first past AA patient, the tumor region of the second digitized H&E training slide image comprises a plurality of individual cells of the second past AA patient, the tumor region of the third digitized H&E training slide image comprises a plurality of individual cells of the first past CA patient, the tumor region of the fourth digitized H&E training slide image comprises a plurality of individual cells of the second past CA patient, and so forth. In some embodiments, the plurality of individual cells of the past AA patients are referred to as the plurality of AA cells, and the plurality of individual cells of the past CA patients are referred to as the plurality of CA cells. The third operation 906 is substantially the same as the second operation 704 described herein.

At the fourth operation 908, each of the individual cells are classified as one cell type of a plurality of cell types. The plurality of cell types comprises tumor-infiltrating lymphocytes (TILs), non-lymphocyte cells, and cancer cells. The fourth operation 908 is substantially the same as the third operation 706.

At the fifth operation 910, for each of the corresponding plurality of individual cells, one or more clusters of stromal TILs and one or more clusters of epithelial TILs are generated. For example, one or more clusters of AA stromal TILs and one or more clusters of AA epithelial TILs are generated for the plurality of AA cells of the first past AA patient, one or more clusters of AA stromal TILs and one or more clusters of AA epithelial TILs are generated for the plurality of AA cells of the second past AA patient, one or more clusters of CA stromal TILs and one or more clusters of CA epithelial TILs are generated for the plurality of CA cells of the first past CA patient, one or more clusters of CA stromal TILs and one or more clusters of CA epithelial TILs are generated for the plurality of CA cells of the second past CA patient, and so forth. The fifth operation 910 is substantially the same as the fourth operation 708. In some embodiments, the method 900 may also comprises defining a boundary for each of the AA cells of each of the corresponding pluralities of AA cells and each of the CA cells of each of the corresponding pluralities of CA cells (see, e.g., third operation 106 of the method 100 of FIG. 1).

At the sixth operation 912, for each of the corresponding plurality of individual cells, a first plurality of architectural features are extracted from the one or more clusters of stromal TILs. In other words, for each of the corresponding plurality of individual cells, a first plurality of architectural features are extracted from the digitized H&E training slide images, where the first plurality of architectural features are at least partially based on corresponding ones of the one or more clusters of stromal TILs.

For example, a first plurality of architectural features are extracted from the one or more clusters of stromal TILs (AA stromal TILs) that were generated for the first past AA patient, a first plurality of architectural features are extracted from the one or more clusters of stromal TILs (AA stromal TILs) that were generated for the second past AA patient, a first plurality of architectural features are extracted from the one or more clusters of stromal TILs (CA stromal TILs) that were generated for the first past CA patient, a first plurality of architectural features are extracted from the one or more clusters of stromal TILs (CA stromal TILs) that were generated for the second past CA patient, and so forth. In some embodiments, the first plurality of architectural features are collectively referred to as (e.g., each of the first plurality of architectural features are collectively referred to as) first pluralities of architectural features. The sixth operation 912 is substantially the same as the fifth operation 710.

At the seventh operation 914, for each of the corresponding plurality of individual cells, a second plurality of architectural features are extracted from the one or more clusters of epithelial TILs. In other words, for each of the corresponding plurality of AA cells, a second plurality of architectural features are extracted from the digitized H&E training slide images, where the second plurality of architectural features are at least partially based on corresponding ones of the one or more clusters of epithelial TILs.

For example, a second plurality of architectural features are extracted from the one or more clusters of epithelial TILs (AA epithelial TILs) that were generated for the first past AA patient, a second plurality of architectural features are extracted from the one or more clusters of epithelial TILs (AA epithelial TILs) that were generated for the second past AA patient, a second plurality of architectural features are extracted from the one or more clusters of epithelial TILs (CA epithelial TILs) that were generated for the first past CA patient, a second plurality of architectural features are extracted from the one or more clusters of epithelial TILs (CA epithelial TILs) that were generated for the second past CA patient, and so forth. In some embodiments, the second plurality of architectural features are collectively referred to as second pluralities of architectural features. The seventh operation 914 is substantially the same as the sixth operation 712.

In some embodiments, for each of the corresponding plurality of individual cells, other pluralities of architectural features are extracted from the digitized H&E training slide images. For example, in some embodiments, a fourth plurality of architectural features are extracted from one or more clusters of cancer cells (and/or non-lymphocyte cells) that were generated for the first past AA patient, a fourth plurality of architectural features are extracted from one or more clusters of cancer cells (and/or non-lymphocyte cells) that were generated for the second past AA patient, a fourth plurality of architectural features are extracted from one or more clusters of cancer cells (and/or non-lymphocyte cells) that were generated for the first past CA patient, a fourth plurality of architectural features are extracted from one or more clusters of cancer cells (and/or non-lymphocyte cells) that were generated for the second past CA patient, and so forth. In such embodiments, it will be appreciated that, for each corresponding plurality of individual cells one or more clusters of cancer cells and/or one or more clusters of non-lymphocyte cells are generated (e.g., in a substantially similar manner as generating the one or more clusters of stromal TILs and the one or more clusters of epithelial TILs).

At the eighth operation 916, the first pluralities of architectural features and the second pluralities of architectural features are refined to a third plurality of architectural features. The architectural features of the third plurality of architectural features are more relevant to predicting OS of the AA patients than the other architectural features of the first pluralities of architectural features and the second pluralities of architectural features. Since the third plurality of architectural features are more relevant to predicting OS of the AA patients than the other architectural features of the first pluralities of architectural features and the second pluralities of architectural features, the third plurality of architectural features are more predicative of OS of the AA patients than OS of the CA patients. In other words, the third plurality of architectural features are more predictive of OS in AA patients than in CA patients.

For example, each of the first pluralities of architectural features may comprise 40 different architectural features that were extracted from the one or more clusters of stromal TILs of a corresponding patient (e.g., a corresponding patient from the training cohort). Likewise, each of the second pluralities of architectural features may comprise 45 different architectural features that were extracted from the one or more clusters of epithelial TILs of a corresponding patient (e.g., a corresponding patient from the training cohort). In other words, for each of the AA patients and each of the CA patients (training cohort patients), 85 different architectural features may be extracted from each of the digitized H&E training slide images (e.g., 40 different architectural features from clusters of stromal TILs and 45 different architectural features from clusters of epithelial TILs). The architectural features of the third plurality of architectural features are more relevant to OS of the AA patients than the other architectural features of the first pluralities of architectural features and the second pluralities of architectural features.

A feature selection process determines which architectural features of the patients are more relevant to OS of the AA patients than the other architectural features of the first pluralities of architectural features and the second pluralities of architectural features. In some embodiments, the feature selection process may be, for example, LASSO, LASSO Cox regression, MCRM mRMR, best subsets selection, correlation feature selection, or the like. In further embodiments, the feature selection is MCRM. In embodiments in which the feature selection is MCRM, the third plurality of architectural features may be more relevant than another, different refined plurality of architectural features of the second and third pluralities of architectural features which were selected by a different feature selection process (e.g., best subsets). In further embodiments, refining the first pluralities of architectural features and the second pluralities of architectural features to the third plurality of architectural features includes acquiring electronic data, reading from a computer file, receiving a computer file, reading from a computer memory, or other computerized activity not practically performed in the human mind.

In some embodiments, the third plurality of architectural features comprises architectural features from only the first plurality of architectural features. In other words, each of the architectural features of the third plurality of architectural features corresponds to only one of the architectural features of the first plurality of architectural features. More specifically, each of the architectural features of the third plurality of architectural features corresponds to an architectural feature that was extracted from the one or more clusters of stromal TILs. For example, the first plurality of architectural features is extracted from each of the past patients. Each of the architectural features of the first plurality of architectural features are based on the one or more clusters of stromal TILs of a corresponding past patient. The architectural features of the third plurality of architectural features may only comprise architectural features of the first plurality of architectural features and not any architectural features of the second plurality of architectural features, which also were extracted from each of the past patients.

In some embodiments, a fifth plurality of architectural features, which are refined from the first and second pluralities of architectural features, are different than the third plurality of architectural features. In further embodiments, the fifth plurality of architectural features are more relevant to OS of the CA patients than the third plurality of architectural features. In further embodiments, the third plurality of architectural features are more relevant to the OS of the AA patients than the fifth plurality of architectural features. In yet further embodiments, none of the architectural features of the third plurality of architectural features are in the fifth plurality of architectural features. In other embodiments, one or more, but less than all, of the architectural features of the third plurality of architectural features are in the fifth plurality of architectural features.

In some embodiments, the third plurality of architectural features comprises at least four architectural features of the one or more clusters of stromal TILs. In some embodiments, the third plurality of architectural features consists of four architectural features of the one or more clusters of stromal TILs. In some embodiments, the fifth plurality of architectural features comprises seven architectural features of the one or more clusters of epithelial TILs. In other embodiments, the fifth plurality of architectural features comprises six architectural features of the one or more clusters of epithelial TILs. The eighth operation 916 is substantially the same as the seventh operation 714.

At the ninth operation 918 risk scores are generated for the AA patients, respectively. For example, a first risk score is generated for the first past AA patient, a second risk score is generated for the second past AA patient, a third risk score is generated for the first past CA patient, a fourth risk score is generated for the second past CA patient, and so forth. Each of the risk scores is generated based on a corresponding third plurality of architectural features. The ninth operation 918 is substantially similar to the eighth operation 716.

At the tenth operation 920, the machine learning classifier is trained based, at least in part, on the risk scores of the patients. In some embodiments, the machine learning classifier is trained to generate a classification of the AA patient (the AA POI) into either a responder group or a non-responder group (see, e.g., the method 200 of FIG. 2). In some embodiments, the machine learning classifier is trained to predict whether the EC of the AA patient (the EC of the AA POI) is either an aggressive subtype of EC or a non-aggressive subtype of EC (see, e.g., the method 400 of FIG. 4). In such embodiments, the first operation 902 comprises training a machine learning classifier to predict whether the EC of the AA patient (the EC of the AA POI) is either an aggressive subtype of EC or a non-aggressive subtype of EC. In some embodiments, the machine learning classifier may be trained to generate a risk group classification of the AA patient (the AA POI) (see, e.g., the method 100 of FIG. 1). In such embodiments, the first operation 902 comprises training a machine learning classifier to generate a risk group classification of the AA patient (the AA POI). The tenth operation 920 is substantially similar to the ninth operation 718.

At the eleventh operation 922, the machine learning classifier is validated on a validation dataset of digitized H&E slide images. The validation dataset comprises a plurality of digitized H&E validation slide images. Each of the plurality of digitized H&E validation slide images demonstrates tissue from a uterus of a corresponding patient and a portion of a gynecologic tumor of the corresponding patient. Further, each of the plurality of digitized H&E validation slide images is associated with a past patient that has EC.

Further, the validation dataset and the training dataset are portions of an original dataset (e.g., a larger collection of digitized H&E slide images). The original dataset comprises a plurality of original digitized H&E slide images. Each of the plurality of original digitized H&E slide images demonstrates tissue from a uterus of a corresponding patient and a portion of a gynecologic tumor of the corresponding patient (both CA patients and AA patients). Further, each of the plurality of original digitized H&E slide images is associated with a past patient that has EC. The original dataset is partitioned into the validation dataset and the training dataset.

In some embodiments, the original dataset is partitioned into the validation dataset and the training dataset by randomly placing the original digitized H&E slide images into either the validation dataset or the training dataset. In some embodiments, the original dataset is partitioned into the validation dataset and the training dataset while maintaining population balance between CA patients and AA patients.

The machine learning classifier is validated on the validation dataset. In some embodiments, the machine learning classifier is validated on the validation dataset to ensure that the machine learning classifier is adequately able to predict a response of the AA patient (the AA POI) to a treatment plan for EC (e.g., generate a classification of the AA patient (AA POI) into either the responder group or non-responder group). In some embodiments, the machine learning classifier is validated on the validation dataset to ensure that the machine learning classifier is adequately able to predict whether the EC of the AA patient (the EC of the AA POI) is either an aggressive subtype of EC or a non-aggressive subtype of EC. In some embodiments, the machine learning classifier is validated on the validation dataset to ensure that the machine learning classifier is adequately able to generate a risk group classification of the AA patient (the AA POI). In some embodiments, a k-fold cross-validation is utilized to validate the machine learning classifier. In further embodiments, a 10-fold cross-validation is utilized to validate the machine learning classifier. It will be appreciated that, in other embodiments, other cross-validation techniques may be utilized to validate the machine learning classifier. The eleventh operation 922 is substantially similar to the tenth operation 720.

Example Use Case 1

An example embodiment includes training a machine learning classifier (e.g., prognostic classifier) to predict OS of an AA patient (e.g., generate a risk group classification for the AA POI).

Methods

In this example, digitized H&E slide images from 445 post-surgery endometrial cancer (EC) patients were chosen for this study. The digitized H&E slide images from the 445 post-surgery EC were chosen from The Cancer Genome Atlas (TCGA). The 445 post-surgery EC had further chemotherapy and/or radiotherapy for their EC. Further, the 445 post-surgery EC had their races reported as either African American (AA) or Caucasian American (CA).

The digitized H&E slide images from the 445 post-surgery EC define a dataset. The dataset was divided into a discovery set (D1, n=300) and a validation set (D2, n=145), while ensuring population balance between the two splits (D1(AA)=65, D1(CA)=235, D2(AA)=37, D2(CA)=108).

Figure 10:
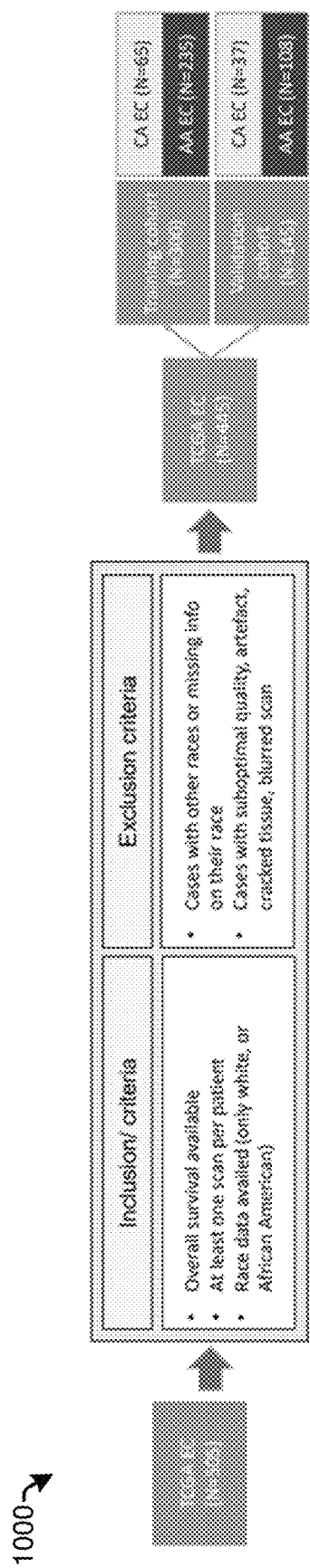
FIG. 10 illustrates a graphical representation of the criteria of a dataset for Example Use Case 1.

FIG. 10 illustrates a graphical representation 1000 of the criteria of the dataset for Example Use Case 1. More specifically, the graphical representation 1000 of FIG. 10 illustrates the criteria for including patients in the Example Use Case 1, the distribution of racial groups in the dataset, and the discovery/validation split (training/validation cohort) for the dataset. It will be appreciated that the graphical representation 1000 of FIG. 10 may be an embodiment of the training dataset of the first operation 902.

A machine learning approach was employed to identify tumor regions, and tumor-associated stroma on the diagnostic slides and then used to automatically identify TILs within these compartments. Graph network theory based computational algorithms were used to capture 85 quantitative descriptors of the architectural patterns of intratumoral and stromal TILs. A multivariable Cox regression model (MCRM) was used to create population specific-prognostic models ($M_{AA}$, $M_{CA}$) and a population-agnostic model ($M_{AA+CA}$) to predict OS. All 3 models were evaluated on D2(AA), D2(CA), and D2(AA+CA).

Figure 11:
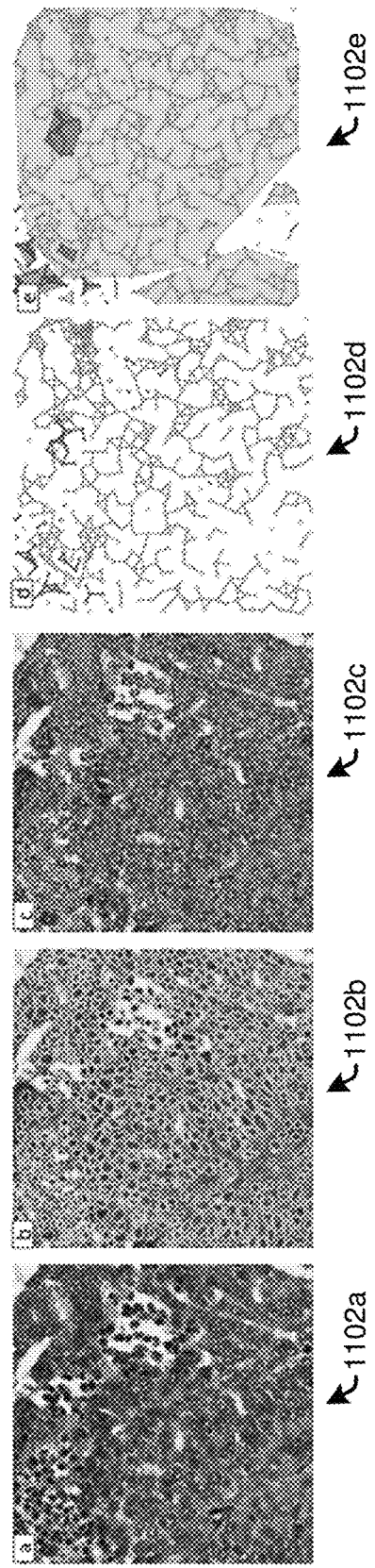
FIG. 11 illustrates a graphical representation of some embodiments for quantifying TIL arrangements for Example Use Case 1.

FIG. 11 illustrates a graphical representation 1100 of some embodiments for quantifying TIL arrangements for Example Use Case 1 (e.g., clusters of stromal TILs, clusters of cancer cells, clusters of intratumoral TILs, etc.). The graphical representation 1100 of FIG. 11 illustrates a first image 1102a that illustrates an enlarged area (e.g., enlarged at 40X) of one of the digitized H&E slide images. The graphical representation 1100 of FIG. 11 illustrates a second image 1102b that illustrates cell boundary segmentation and classification into tumor-infiltrating lymphocytes (yellow) and cancer cells (cyan). The graphical representation 1100 of FIG. 11 illustrates a third image 1102c that illustrates overlaid clusters of proximal cells constructed by graph theory. The graphical representation 1100 of FIG. 11 illustrates a fourth image 1102d that illustrates arranging clusters into subgraphs of TILs (red) and cancer cell foci (green) that may interact in the tumor microenvironment. The graphical representation 1100 of FIG. 11 illustrates a fifth image 1102e that illustrates a convex hull of cell clusters and calculating of the overlapped area. It will be appreciated that the graphical representation 1100 of FIG. 11 may be an embodiment of one or more of the operations of the method 900 of FIG. 9.

Figure 12:
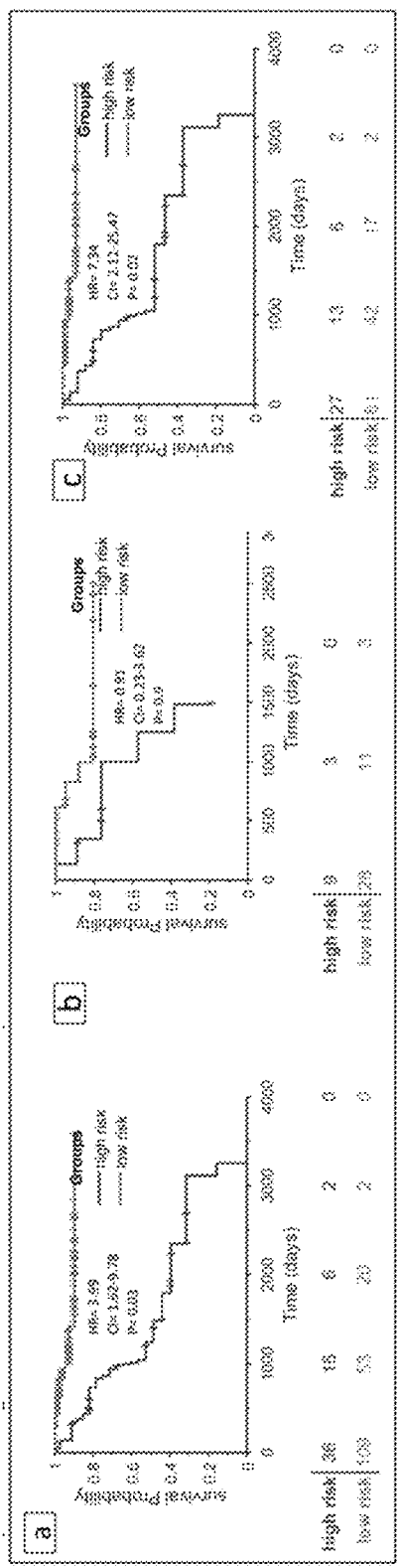
FIG. 12 illustrates various plots associated with survival analysis results for a population-agnostic model ($M_{AA+CA}$) of the Example Use Case 1.

FIG. 12 illustrates various plots associated with survival analysis results for the population-agnostic model ($M_{AA+CA}$) of the Example Use Case 1. More specifically, FIG. 12 illustrates a first, second, and third Kaplan-Meier survival curves 1202a-1202c for the population-agnostic model ($M_{AA+CA}$) of the Example Use Case 1. The first Kaplan-Meier survival curve 1202a illustrates a survival analysis of the population-agnostic model ($M_{AA+CA}$) on the AA+CA cohort. The second Kaplan-Meier survival curve 1202b illustrates a survival analysis of the population-agnostic model ($M_{AA+CA}$) on the AA cohort. The third Kaplan-Meier survival curve 1202c illustrates a survival analysis of the population-agnostic model ($M_{AA+CA}$) on the CA cohort. As shown in FIG. 12, the population-agnostic model ($M_{AA+CA}$) was predicative of OS on the CA cohort (and the AA+CA cohort), but not prognostic on the AA cohort. It will be appreciated that the various plots of FIG. 12 may be representative of some embodiments of the method 900 of FIG. 9.

Figure 13:
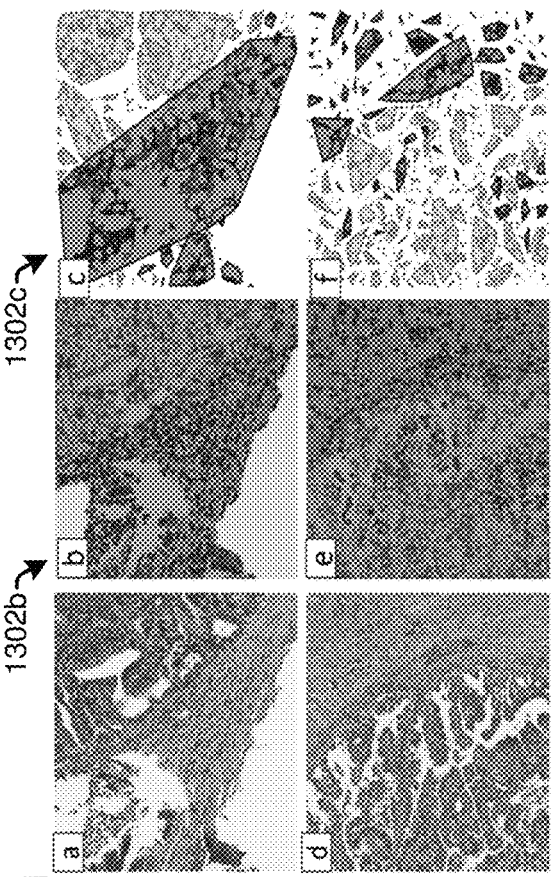
FIG. 13 illustrates digitized H&E slide images of a long-term patient and digitized H&E slide images of a short-term patient of the Example Use Case 1.

FIG. 13 illustrates digitized H&E slide images of a long-term patient and digitized H&E slide images of a short-term patient of the Example Use Case 1. More specifically, FIG. 13 illustrates a first image 1302a, a second image 1302b, and a third image 1302c that are associated with the long-term patient, and a fourth image 1302d, a fifth image 1302e, and a sixth image 1302f that are associated with the short-term patient.

The first image 1302a illustrates an area (e.g., enlarged area) of a digitized H&E slide image of the long-term patient (e.g., a patient that died on or after a threshold date) of the dataset. The second image 1302b illustrates cell boundary segmentation and classification of individual cells of the digitized H&E slide image of the long-term patient. The third image 1302c illustrates the formation of clusters of the individual cells of the digitized H&E slide image of the long-term patient.

The fourth image 1302d illustrates an area (e.g., enlarged area) of a digitized H&E slide image of the short-term patient (e.g., a patient that died before the threshold date) of the dataset. The fifth image 1302e illustrates cell boundary segmentation and classification of individual cells of the digitized H&E slide image of the short-term patient. The sixth image 1302f illustrates the formation of clusters of the individual cells of the digitized H&E slide image of the short-term patient.

In FIG. 13, cyan illustrates stromal TILs (and clusters), blue illustrates non-TIL cells (and clusters), orange illustrates epithelial TILs (and clusters), and green illustrates cancer cells (and clusters). As shown in FIG. 13, the clusters of cells of the long-term patient and the short-term patient are significantly different. It will be appreciated that the various images of FIG. 13 may be representative of some embodiments of the method 900 of FIG. 9.

Figure 14:
FIG. 14 illustrates digitized H&E slide images of a long-term surviving AA patient and digitized H&E slide images of a short-term surviving AA patient for Example Use Case 1.

FIG. 14 illustrates digitized H&E slide images of a long-term surviving AA patient and digitized H&E slide images of a short-term surviving AA patient for Example Use Case 1. More specifically, FIG. 14 illustrates a first image 1402a, a second image 1402b, and a third image 1402c that are associated with the long-term surviving AA patient, and a fourth image 1402d, a fifth image 1402e, and a sixth image 1402f that are associated with the short-term surviving AA patient.

The first image 1402a illustrates an area (e.g., enlarged area) of a digitized H&E slide image of the long-term surviving AA patient. The second image 1402b illustrates cell boundary segmentation and classification of individual cells of the digitized H&E slide image of the long-term surviving AA patient. The third image 1402c illustrates the formation of clusters of the individual cells of the digitized H&E slide image of the long-term surviving AA patient.

The fourth image 1402d illustrates an area (e.g., enlarged area) of a digitized H&E slide image of a short-term surviving AA patient. The fifth image 1402e illustrates cell boundary segmentation and classification of individual cells of the digitized H&E slide image of the short-term surviving AA patient. The sixth image 1402f illustrates the formation of clusters of the individual cells of the digitized H&E slide image of the short-term surviving AA patient.

In FIG. 14, cyan illustrates stromal TILs (and clusters), blue illustrates stromal non-lymphocyte cells (and clusters), green illustrates epithelial TILs (and clusters), orange illustrates cancer cells (and clusters). As shown in FIG. 14, the clusters of cells (e.g., clusters of stromal TILs) of the long-term surviving AA patient and the short-term surviving AA patient are significantly different. It will be appreciated that the various images of FIG. 14 may be representative of some embodiments of the method 900 of FIG. 9.

Figure 15:
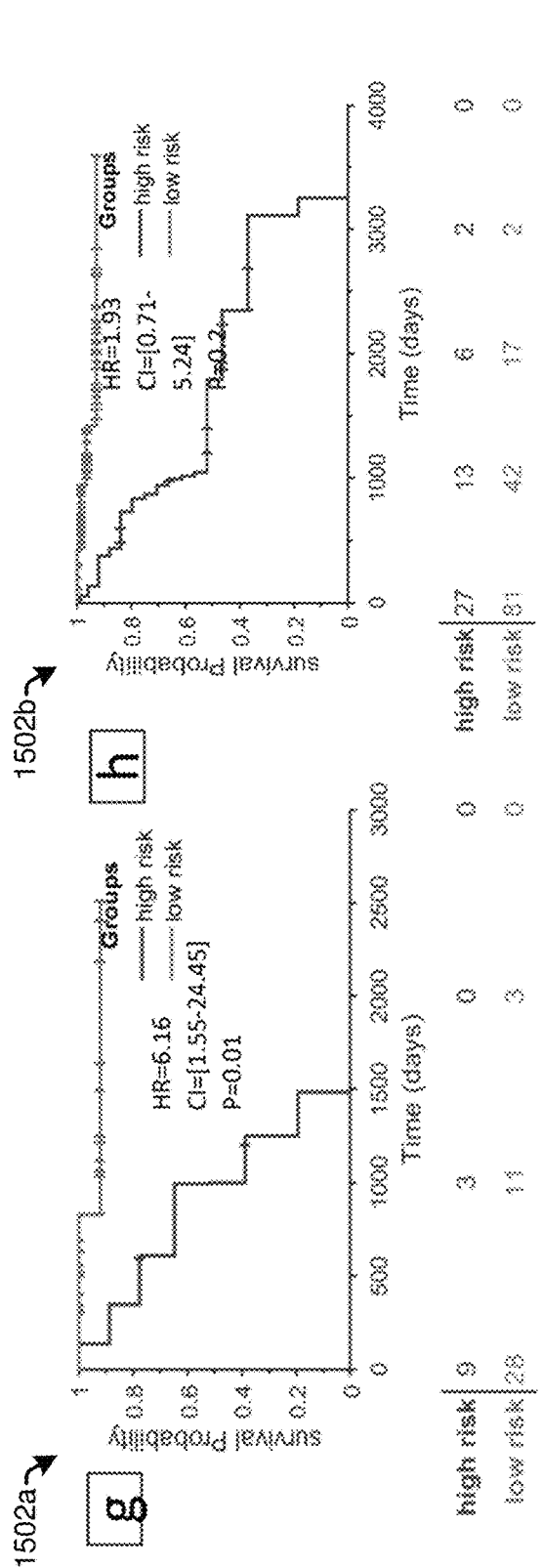
FIG. 15 illustrates various plots associated with survival analysis results for population-specific models (($M_{AA}$) and ($M_{CA}$)) of the Example Use Case 1.

FIG. 15 illustrates various plots associated with survival analysis results for the population-specific models (($M_{AA}$) and ($M_{CA}$)) of the Example Use Case 1. More specifically, FIG. 15 illustrates a first Kaplan-Meier survival curve 1502a and a second Kaplan-Meier survival curve 1502b for the population-specific models (($M_{AA}$) and ($M_{CA}$)) of the Example Use Case 1. The first Kaplan-Meier survival curve 1502a illustrates a survival analysis of the AA population-specific model ($M_{AA}$) on the AA cohort. The second Kaplan-Meier survival curve 1502b illustrates a survival analysis of the AA population-specific model ($M_{AA}$) on the CA cohort. As shown in FIG. 15, the AA population-specific model ($M_{AA}$) is prognostic on the AA cohort but not the CA cohort. It will be appreciated that the various plots of FIG. 15 may be representative of some embodiments of the method 900 of FIG. 9.

Figure 16:
FIG. 16 illustrates digitized H&E slide images of a long-term surviving CA patient and digitized H&E slide images of a short-term surviving CA patient for Example Use Case 1.
Figure 16:
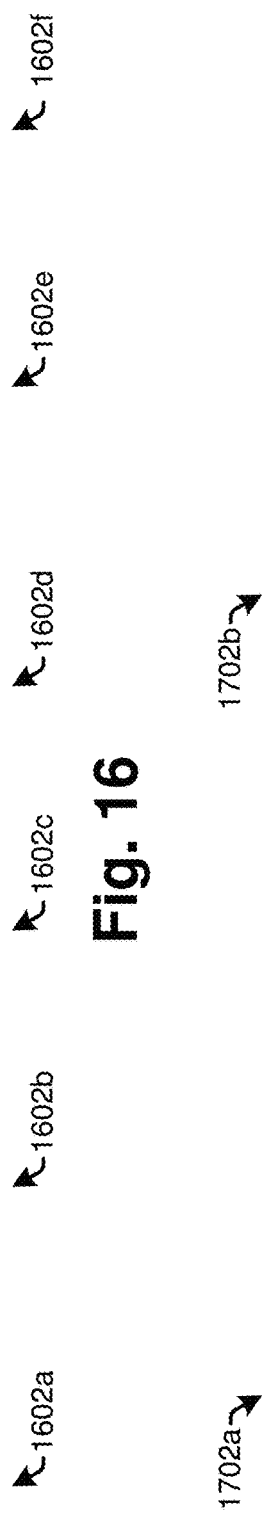

FIG. 16 illustrates digitized H&E slide images of a long-term surviving CA patient and digitized H&E slide images of a short-term surviving CA patient for Example Use Case 1. More specifically, FIG. 16 illustrates a first image 1602a, a second image 1602b, and a third image 1602c that are associated with the long-term surviving CA patient, and a fourth image 1602d, a fifth image 1602e, and a sixth image 1602f that are associated with the short-term surviving CA patient.

The first image 1602a illustrates an area (e.g., enlarged area) of a digitized H&E slide image of the long-term surviving CA patient (e.g., a CA patient that died on or after a threshold date). The second image 1602b illustrates cell boundary segmentation and classification of individual cells of the digitized H&E slide image of the long-term surviving CA patient. The third image 1602c illustrates the formation of clusters of the individual cells of the digitized H&E slide image of the long-term surviving CA patient.

The fourth image 1602*d* illustrates an area (e.g., enlarged area) of a digitized H&E slide image of a short-term surviving CA patient (e.g., a CA patient that died before the threshold date). The fifth image 1602*e* illustrates cell boundary segmentation and classification of individual cells of the digitized H&E slide image of the short-term surviving CA patient. The sixth image 1602*f* illustrates the formation of clusters of the individual cells of the digitized H&E slide image of the short-term surviving CA patient.

In FIG. 16, cyan illustrates stromal TILs (and clusters), blue illustrates stromal non-lymphocyte cells (and clusters), green illustrates epithelial TILs (and clusters), orange illustrates cancer cells (and clusters). As shown in FIG. 16, the clusters of cells (e.g., clusters of stromal TILs) of the long-term surviving CA patient and the short-term surviving CA patient are significantly different. It will be appreciated that the various images of FIG. 16 may be representative of some embodiments of the method 900 of FIG. 9.

Figure 17:
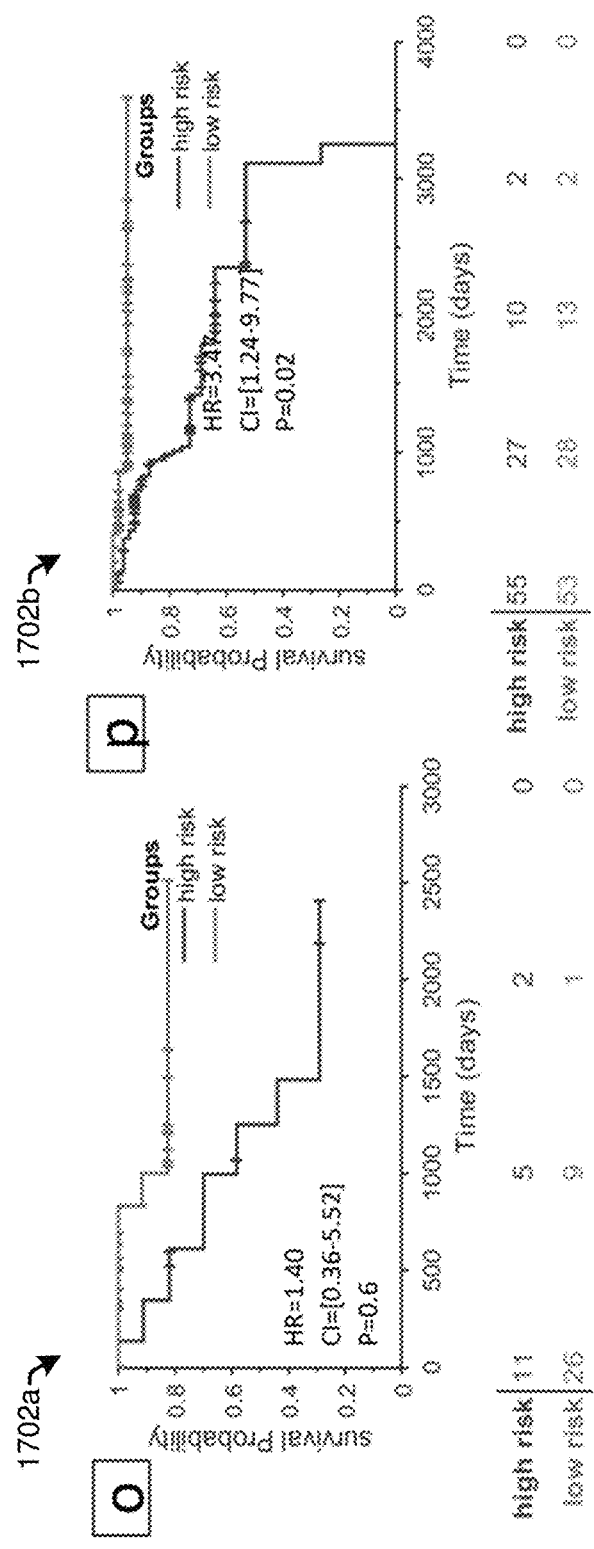
FIG. 17 illustrates various plots associated with survival analysis results for the population-specific models (($M_{AA}$) and ($M_{CA}$)) of the Example Use Case 1.

FIG. 17 illustrates various plots associated with survival analysis results for the population-specific models (($M_{AA}$) and ($M_{CA}$)) of the Example Use Case 1. More specifically, FIG. 17 illustrates a first Kaplan-Meier survival curve 1702*a* and a second Kaplan-Meier survival curve 1702*b* for the population-specific models (($M_{AA}$) and ($M_{CA}$)) of the Example Use Case 1. The first Kaplan-Meier survival curve 1702*a* illustrates a survival analysis of the CA population-specific model ($M_{CA}$) on the AA cohort. The second Kaplan-Meier survival curve 1702*b* illustrates a survival analysis of the CA population-specific model ($M_{CA}$) on the CA cohort. As shown in FIG. 17, the CA population-specific model ($M_{CA}$) is prognostic on the CA cohort but not the AA cohort. It will be appreciated that the various plots of FIG. 17 may be representative of some embodiments of the method 900 of FIG. 9.

Results $M_{AA}$ identified 4 prognostic features relating to interaction(s) of TIL clusters with cancer nuclei in the stromal compartment and was prognostic of OS on D2(AA) (see, Table 1), but not prognostic in D2(CA) nor D2(AA+CA). $M_{CA}$ and $M_{AA+CA}$ identified respectively 7 and 6 prognostic features relating to interaction(s) of TIL clusters with cancer nuclei (both in the epithelial and stromal regions) and were prognostic of OS on D2(CA) and D2(AA+CA), but not prognostic in D2(AA).

due to the single classification being displayed) determine the time in which the AA patient has to live. Accordingly, the medical practitioner may be able to accurately guide the EC treatment of the AA patient to achieve better treatment results (e.g., expedite alternative treatment options (e.g., adjuvant therapy), choose a less aggressive treatment plan to reduce negative side effects, etc.). Further, the medical practitioner may be able to provide better care to the AA patient (e.g., improve patient satisfaction and/or knowledge) by being able to better predict life expectancy and provide this information to the AA patient. Embodiments thus provide a measurable improvement over existing methods, systems, apparatus, or other devices in improving the treatment of AA patients with EC.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods or operations 100, 200, 300, 400, 500, 600, 700, 800, 900, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to generating the risk group classification of the AA patient are based on architectural features that may not be perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images

TABLE 1

|  | $M_{AA}$ | | | $M_{AA+CA}$ | | | $M_{CA}$ | | |
| --- | --- | --- | --- | --- | --- | --- | --- | --- | --- |
|  | HR | CI | P | HR | CI | P | HR | CI | P |
| D2(AA) | 6.16 | 1.55-24.45 | 0.01 | 0.91 | 0.23-3.62 | 0.9 | 1.40 | 0.36-5.52 | 0.6 |
| D2 | 2.12 | 0.94-4.77 | 0.07 | 3.99 | 1.62-9.78 | 0.03 | 2.38 | 1.07-5.31 | 0.03 |
| D2(CA) | 1.93 | 0.71-5.24 | 0.2 | 7.34 | 2.12-25.47 | 0.02 | 3.47 | 1.24-9.77 | 0.02 |

Figure 18:
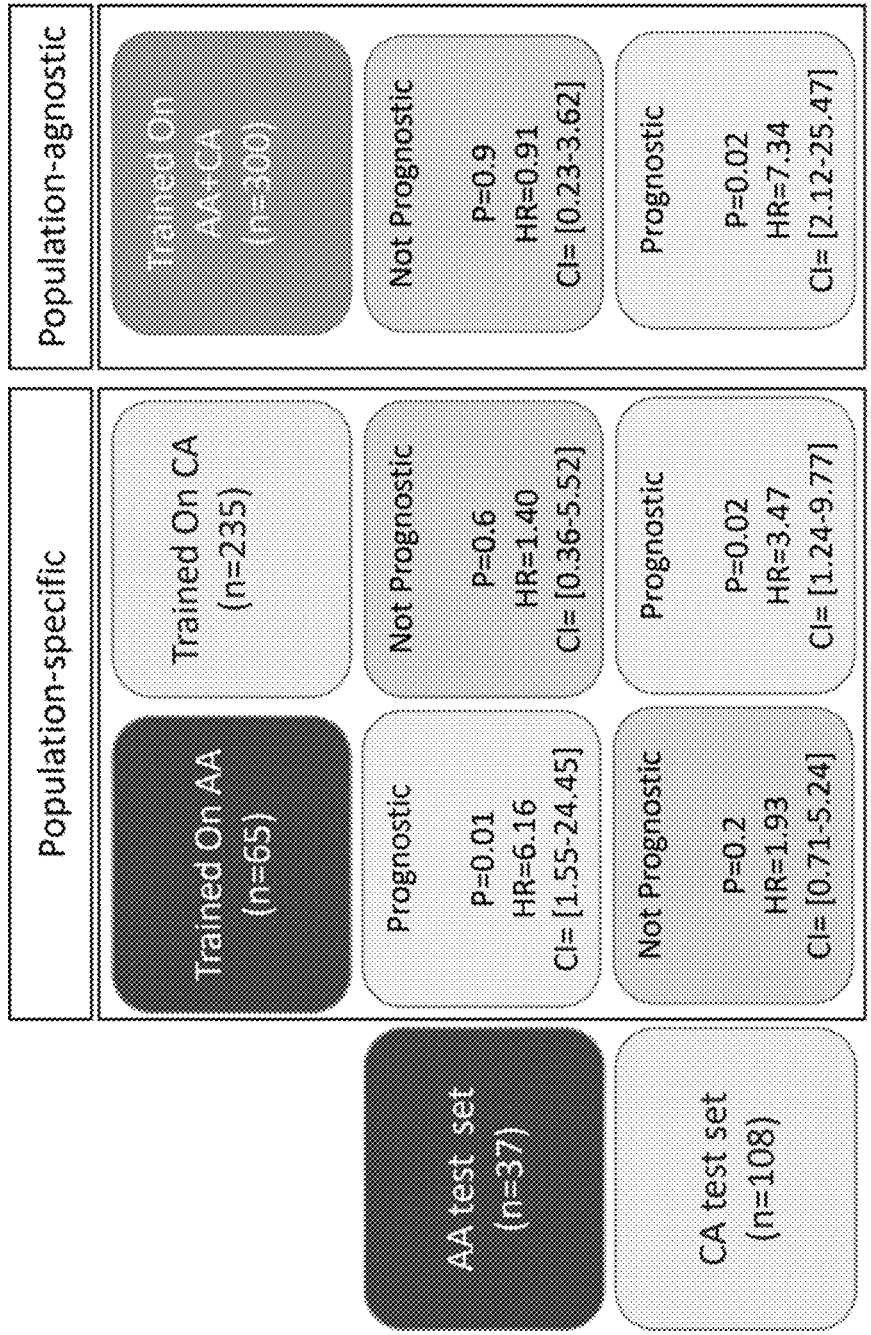
FIG. 18 illustrates a graphical representation of an overview of the results of Example Use Case 1.

FIG. 18 illustrates a graphical representation 1800 of an overview of the results of Example Use Case 1.

Conclusion

As described herein, stromal TIL architecture are more prognostic of OS in AA women with EC, while epithelial TIL features were more prognostic in CA women.

As demonstrated by the example embodiments, various embodiments can facilitate classifying a AA patient into either a high risk group or a low risk group based on a risk score of the AA patient. By being able to classify the AA patient into either the high risk group or the low risk group based on the risk score of the AA patient, a medical practitioner may be able to easily and timely (e.g., intuitively stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 19:
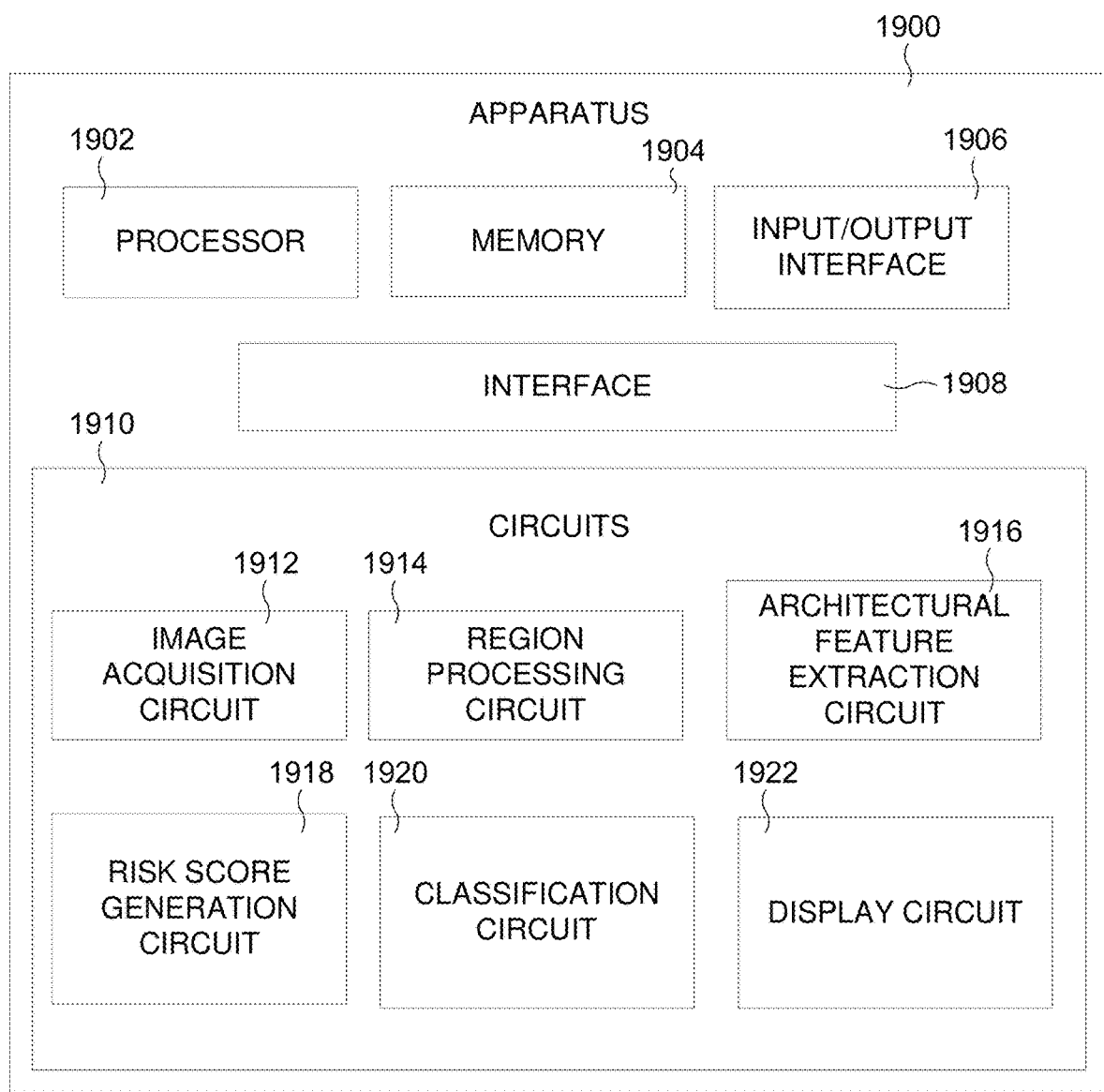
FIG. 19 illustrates some embodiments of an apparatus that can facilitate the methods described herein.

FIG. 19 illustrates some embodiments of an apparatus that can facilitate the methods described herein. For example, FIG. 19 illustrates some embodiments of an apparatus 1900 that can facilitate classifying a new AA patient into a high risk group or a low risk group based on architectural features extracted from a digitized H&E slide image of the AA patient, according to various embodiments discussed herein.

Apparatus 1900 may be configured to perform various techniques, operations, or methods discussed herein, for example, training a machine learning classifier (e.g., linear discriminant analysis, quadratic discriminant analysis classifier, support vector machine, etc.) based on a training dataset to classify an AA patient into the high risk group or the low risk group (e.g., generate a risk score classification of the AA patient), employing the trained machine learning classifier to generate a classification of the AA patient into either a responder or non-responder group, and/or employing the trained machine learning classifier to generate a classification of the EC of the AA patient as either an aggressive subtype of EC or a non-aggressive subtype of EC.

In one embodiment, apparatus 1900 includes a processor 1902, and a memory 1904. Processor 1902 may, in various embodiments, include circuitry such as, but not limited to, one or more single-core or multi-core processors. Processor 1902 may include any combination of general-purpose processors and dedicated processors (e.g., graphics processors, application processors, etc.). The processor(s) can be coupled with and/or can comprise memory (e.g., memory 1904) or storage and can be configured to execute instructions stored in the memory 1904 or storage to enable various apparatus, applications, or operating systems to perform operations and/or methods discussed herein.

Memory 1904 is configured to store a digitized H&E slide image of the AA patient. In some embodiments, memory 1904 can also store a training dataset of digitized H&E slide images for training the machine learning classifier (e.g., linear discriminant analysis classifier, etc.), and/or a validation dataset of digitized H&E slide image. Memory 1904 can be further configured to store one or more clinical features (e.g., cancer stage) or other data associated with the AA patient.

Apparatus 1900 also includes an input/output (I/O) interface 1906; a set of circuits 1910; and an interface 1908 that connects the processor 1902, the memory 1904, the I/O interface 1906, and the set of circuits 1910. I/O interface 1906 may be configured to transfer data between memory 1904, processor 1902, circuits 1910, and external devices, for example, an imaging device (e.g., digital microscope).

The set of circuits 1910 includes an image acquisition circuit 1912, a region processing circuit 1914, an architectural feature extraction circuit 1916, a risk score generation circuit 1918, a classification circuit 1920, and a display circuit 1922.

The image acquisition circuit 1912 is configured to access the digitized H&E slide image of the AA patient, according to embodiments and examples described. The image acquisition circuit 1912 may also be configured to access the digitized H&E slide images of the validation dataset and/or training dataset, according to embodiments and examples described. Accessing the digitized H&E slide image may include accessing the digitized H&E slide image stored in memory 1904. In another embodiment accessing the digitized H&E slide image may include acquiring electronic data, reading from a computer file, receiving a computer file, reading from a computer memory, or other computerized activity not practically performed in the human mind.

Region processing circuit 1914 is configured to define a tumor region in the digitized H&E slide image, classify a plurality of individual cells into cell types, classify TILs as stromal TILs or epithelial TILs, and generate one or more clusters of stromal TILs, according to embodiments and examples described.

Architectural feature extraction circuit 1916 is configured to extract a plurality of architectural features from the digitized H&E slide image, according to embodiments and examples described.

Risk score generation circuit 1918 is configured to generate a risk score for the AA patient based on the plurality of architectural features, according to embodiments and examples described. The risk score generation circuit 1918 may also be configured to generate risk scores for the digitized H&E slide images of the validation dataset and/or the digitized H&E slide image of the training dataset, according to embodiments and examples described.

Classification circuit 1920 is configured to generate a risk group classification of the AA patient based on, at least partially, the risk score of the AA patient, according to embodiments and examples described. The classification circuit 1920 may also be configured to generate a risk group classification of past EC patients (e.g., of the validation/training dataset), according to embodiments and examples described.

Display circuit 1922 is configured to display the risk group classification of the AA patient, according to embodiments and examples described. The display circuit 1922 may also be configured to display the classification of past EC patients, according to embodiments and examples described.

Figure 20:
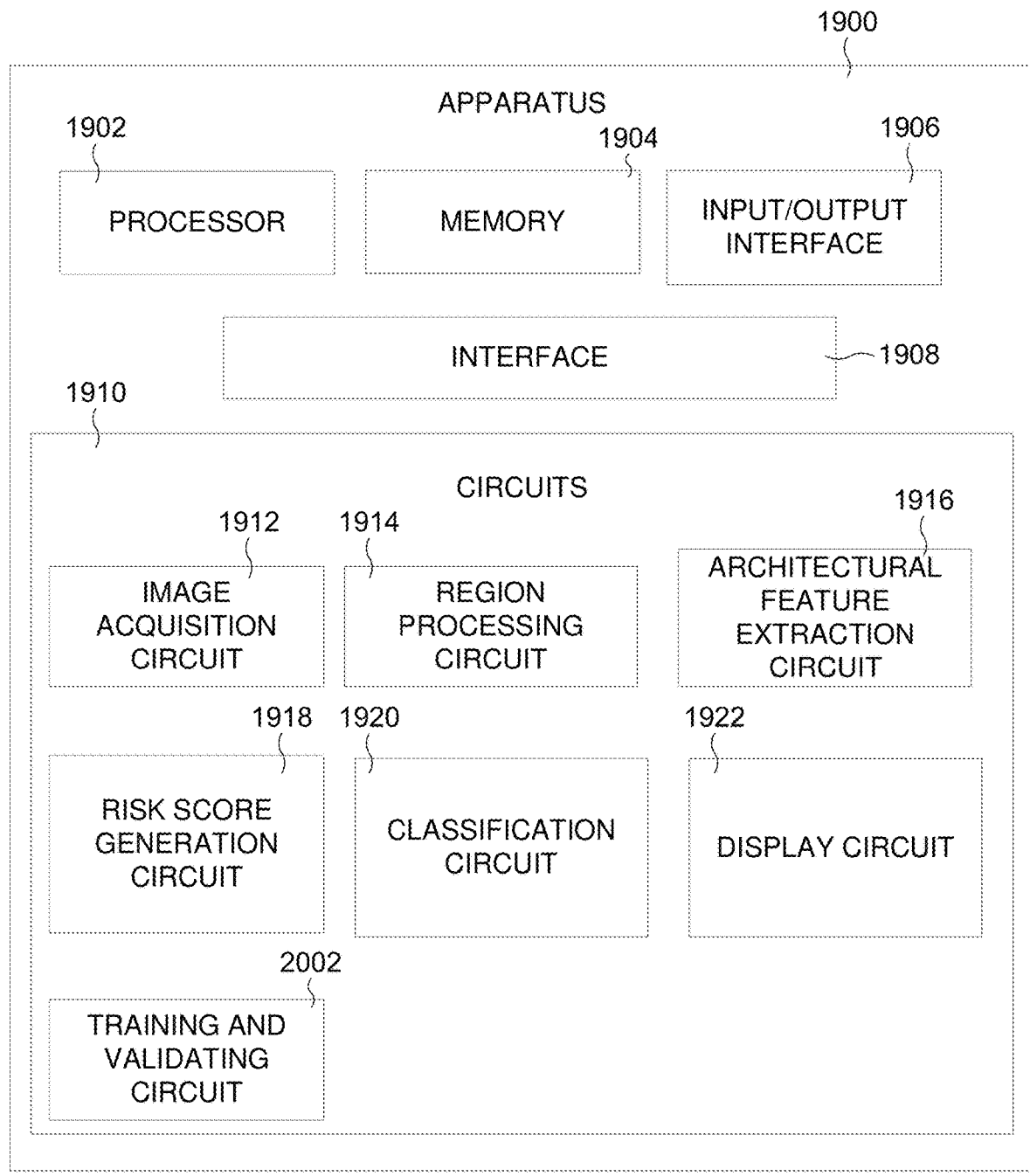
FIG. 20 illustrates some other embodiments of the apparatus of FIG. 19.

FIG. 20 illustrates some other embodiments of the apparatus 1900 of FIG. 19. As shown in FIG. 20, in some embodiments, the set of circuits 1910 further includes a training and validating circuit 2002. The training and validating circuit 2002 is configured to train the classification circuit 1920 on a training dataset (e.g., a training cohort); and optionally validate the classification circuit 1920 on a validation dataset (e.g., a validation cohort), according to various embodiments described herein.

Figure 21:
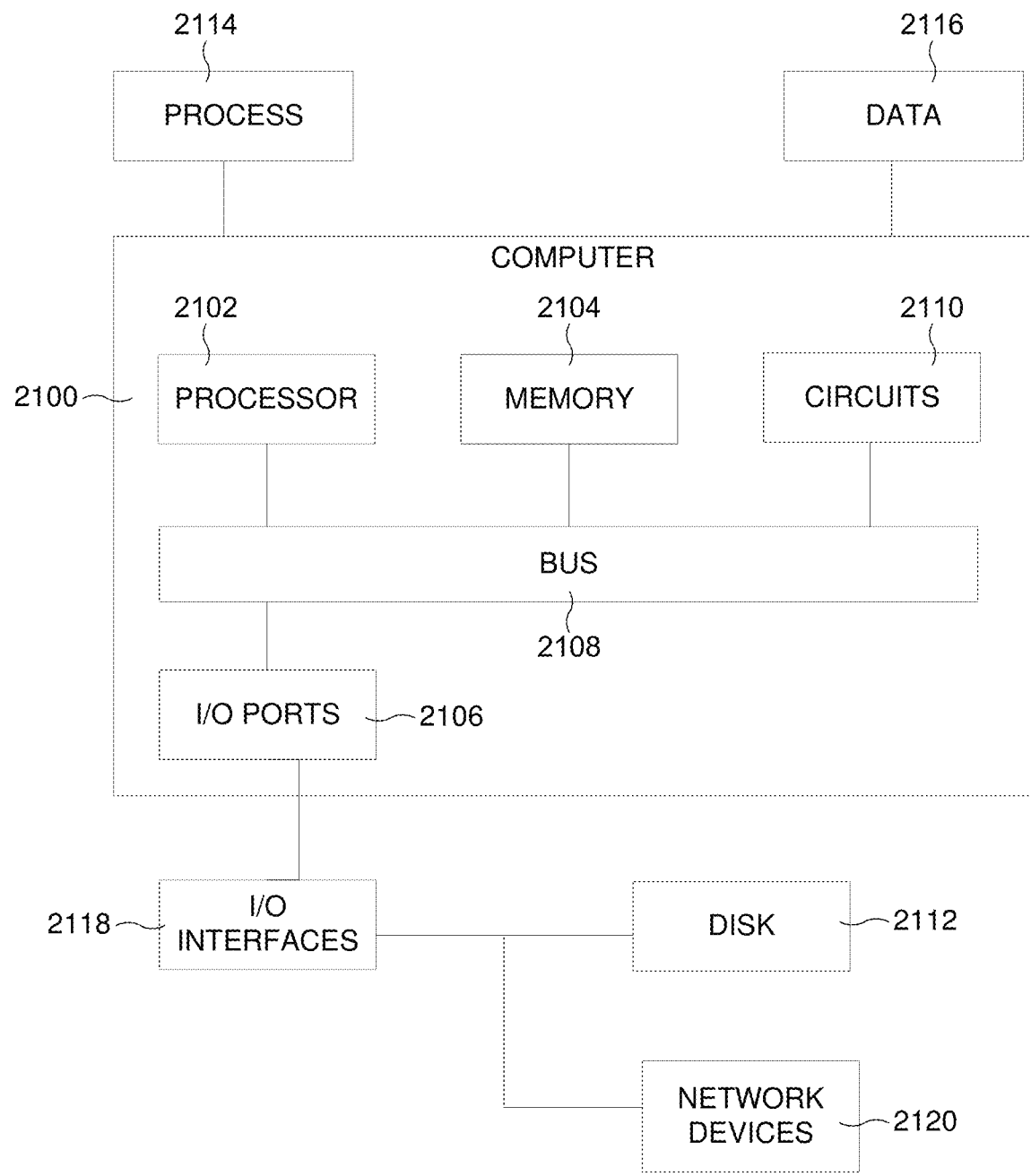
FIG. 21 illustrates some embodiments of a computer in which methods described herein can operate and in which example methods, apparatus, circuits, operations, or logics may be implemented

FIG. 21 illustrates some embodiments of a computer in which methods described herein can operate and in which example methods, apparatus, circuits, operations, or logics may be implemented. In different examples, computer 2100 may be part of an AA patient OS prediction system or an imaging system, or may be operably coupled to an AA patient OS prediction system or an imaging system.

Computer 2100 includes a processor 2102, a memory 2104, and input/output (I/O) ports 2106 operably connected by a bus 2108. In one example, computer 2100 may include a set of logics or circuits 2110 that perform operations for or a method of classifying an AA patient into the high risk group or the low risk group (e.g., generating a risk group classification of the AA patient), generating a classification of the AA patient into either a responder or non-responder group, and/or generating a classification of the EC of the AA patient as either an aggressive subtype of EC or a non-aggressive subtype of EC, according to embodiments and examples described. Thus, the set of circuits 2110, whether implemented in computer 2100 as hardware, firmware, software, and/or a combination thereof may provide means (e.g., hardware, firmware, circuits) for classifying an AA patient into the high risk group or the low risk group (e.g., generating a risk group classification of the AA patient), generating a classification of the AA patient into either a responder or non-responder group, and/or generating a classification of the EC of the AA patient as either an aggressive subtype of EC or a non-aggressive subtype of EC, according to embodiments and examples described. In different examples, the set of circuits 2110 may be permanently and/or removably attached to computer 2100.

Processor 2102 can be a variety of various processors including dual microprocessor and other multi-processor architectures. Processor 2102 may be configured to perform steps of methods claimed and described herein. Memory 2104 can include volatile memory and/or non-volatile memory. A disk 2112 may be operably connected to computer 2100 via, for example, an input/output interface 2118 (e.g., card, device) and an input/output port 2106. Disk 2112 may include, but is not limited to, devices like a magnetic disk drive, a tape drive, a Zip drive, a flash memory card, or a memory stick. Furthermore, disk 2112 may include optical drives like a CD-ROM or a digital video ROM drive (DVD ROM). Memory 2104 can store processes 2114 or data 2116, for example. Data 2116 may, in one embodiment, include digitized H&E slide images, according to embodiments and examples described. Disk 2112 or memory 2104 can store an operating system that controls and allocates resources of computer 2100.

Bus 2108 can be a single internal bus interconnect architecture or other bus or mesh architectures. While a single bus is illustrated, it is to be appreciated that computer 2100 may communicate with various devices, circuits, logics, and peripherals using other buses that are not illustrated (e.g., PCIE, SATA, Infiniband, IEEE 1394, USB, Ethernet).

Computer 2100 may interact with input/output devices via I/O interfaces 2118 and the I/O ports 2106. Input/output devices can include, but are not limited to, MRI systems, CT systems, a keyboard, a microphone, a pointing and selection device, cameras, video cards, displays, disk 2112, network devices 2120, or other devices. The I/O ports 2106 can include but are not limited to, serial ports, parallel ports, or USB ports.

Computer 2100 may operate in a network environment and thus may be connected to network devices 2120 via I/O interfaces 2118 or I/O ports 2106. Through the network devices 2120, computer 2100 may interact with a network. Through the network, computer 2100 may be logically connected to remote computers. The networks with which computer 2100 may interact include, but are not limited to, a local area network (LAN), a wide area network (WAN), or other networks, including the cloud.

Examples herein can include subject matter such as an apparatus, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for classifying an AA patient into the high risk group or the low risk group (e.g., generating a risk group classification of the AA patient), generating a classification of the AA patient into either a responder or non-responder group, and/or generating a classification of the EC of the AA patient as either an aggressive subtype of EC or a non-aggressive subtype of EC, according to embodiments and examples described.

In some embodiments, the present application provides a method. The method comprises accessing a digitized H&E slide image of an African American (AA) patient, wherein the digitized H&E slide image of the AA patient demonstrates one or more indicators of endometrial cancer (EC), and wherein the digitized H&E slide of the AA patient demonstrates tissue from a uterus of the AA patient and at least a portion of a gynecologic tumor. A tumor region is defined in the digitized H&E slide image, wherein the tumor region comprises at least a portion of the gynecologic tumor, and wherein the tumor region comprises a plurality of individual cells. A boundary for each of the plurality of individual cells is defined. The plurality of individual cells are classified into cell types, wherein the cell types comprise tumor-infiltrating lymphocytes (TILs), non-lymphocyte cells, and cancer cells. The TILs are classified as stromal TILs or epithelial TILs. A cluster of stromal TILs are generated, wherein the cluster of stromal TILs comprises a subset of stromal TILs that are related to one another based on proximity. A first plurality of architectural features are extracted from the digitized H&E slide image of the AA patient, wherein each of the first plurality of architectural features are at least partially based on the cluster of stromal TILs. A risk score is generated for the AA patient based on the first plurality of architectural features, wherein the risk score is prognostic of overall survival (OS) of the AA patient. A risk group classification is generated for the AA patient, wherein generating the risk group classification comprises classifying the AA patient into either a high risk group or a low risk group based on the risk score, wherein the high risk group indicates the AA patient will die before a threshold date and the low risk group indicates the AA patient will die after or on the threshold date. The risk group classification of the AA patient is displayed.

In some embodiments, the method further comprises: providing the risk score to a machine learning classifier that is trained to predict a response of the AA patient to a treatment plan for the EC; receiving, from the machine learning classifier, a classification of the AA patient into either a responder group (RG) or a non-responder group (NRG), where the NRG indicates the AA patient will not respond to the treatment plan and the RG indicates that the AA patient will respond to the treatment plan; and displaying the classification of the AA patient as either in the NRG or in the RG.

In some embodiments, the treatment plan comprises at least one of chemotherapy and radiation.

In some embodiments, the method further comprises: extracting a second plurality of architectural features from the digitized H&E slide image of the AA patient, wherein each of the second plurality of architectural features are at least partially based on the cluster of stromal TILs; and selecting a subset of architectural features of the second plurality of architectural features, wherein the subset of architectural features of the second plurality of architectural features are more relevant to predicting OS of AA patients with EC than the other architectural features of the second plurality of architectural features for a predefined feature selection process, and wherein the subset of architectural features defines the first plurality of architectural features.

In some embodiments, selecting the subset of architectural features of the second plurality of architectural features comprises performing a least absolute shrinkage and selection operator (LASSO) technique on the second plurality of architectural features.

In some embodiments, the first plurality of architectural features are based only on the cluster of stromal TILs.

In some embodiments, generating the risk score for the AA patient based on the first plurality of architectural features comprises: assigning a value to each of the architectural features of the first plurality of architectural features; assigning a weighting coefficient to each of the values; and combining the values and their respective weighting coefficients linearly to generate the risk score.

In some embodiments, the cluster of stromal TILs is generated via a graph theory technique.

In some embodiments, classifying the AA patient into either the high risk group or the low risk group comprises comparing the risk score of the AA patient to a threshold value.

In some embodiments, classifying the AA patient into either the high risk group or the low risk group further comprises: classifying the AA patient into the high risk group if the risk score for the AA patient is greater than the threshold value; and classifying the AA patient into the low risk group if the risk score for the AA patient is less than or equal to the threshold value.

In some embodiments, the present application provides a non-transitory computer-readable storage device storing computer-executable instructions that when executed cause a processor to perform operations. The operations comprise: accessing a digitized H&E slide image of an (AA) African American patient, wherein the digitized H&E slide image of the AA patient demonstrates one or more indicators of endometrial cancer (EC), and wherein the digitized H&E slide image of the AA patient demonstrates tissue from a uterus of the AA patient and at least a portion of a gynecologic tumor; defining a tumor region in the digitized H&E slide image of the AA patient, wherein the tumor region comprises at least a portion of the gynecologic tumor, and wherein the tumor region comprises a plurality of individual cells; classifying the plurality of individual cells into cell types, wherein the cell types comprise tumor-infiltrating lymphocytes (TILs) and non-lymphocyte cells; classifying the TILs as intratumoral TILs or stromal TILs; generating one or more clusters of stromal TILs, wherein each of the one or more clusters of stromal TILs comprises a subset of stromal TILs that are related to one another based on proximity; extracting a plurality of architectural features from the digitized H&E slide image of the AA patient, wherein the plurality of architectural features are at least partially based on the one or more clusters of stromal TILs; generating a risk score for the AA patient based on the plurality of architectural features, wherein the risk score is prognostic of overall survival (OS) of the AA patient; providing the risk score to a machine learning classifier that is trained to predict whether the EC of the AA patient is either an aggressive subtype of EC or a non-aggressive subtype of EC; receiving, from the machine learning classifier, a classification of the EC of the AA patient as either the aggressive subtype of EC or the non-aggressive subtype of EC; and displaying the classification of the EC of the AA patient.

In some embodiments, each of the plurality of architectural features corresponds to a different architectural feature of the one or more clusters of stromal TILs.

In some embodiments, generating the risk score comprises: assigning a plurality of values to the plurality of architectural features, respectively, wherein each of the values of the plurality of values corresponds to a number of times a corresponding architectural feature of the plurality of architectural features is present in the digitized H&E slide image of the AA patient; and combining, linearly, the plurality of values with a plurality of weighting coefficients, wherein the plurality of weighting coefficients are attached to the plurality of values, respectively.

In some embodiments, the plurality of architectural features comprises at least four architectural features.

In some embodiments, the plurality of architectural features are based only on the one or more clusters of stromal TILs.

In some embodiments, the plurality of architectural features consists of four architectural features.

In some embodiments, generating the one or more clusters of stromal TILs comprises grouping the stromal TILs into corresponding clusters of the one or more clusters of stromal TILs based on a distance in which the stromal TILs are spaced from one another, wherein each stromal TIL of a given cluster of the one or more clusters of stromal TILs is spaced from a neighboring stromal TIL of the given cluster by less than a threshold distance.

In some embodiments, the present application provides a non-transitory computer-readable storage device storing computer-executable instructions that when executed cause a processor to perform operations. The operations comprising: accessing a training dataset of digitized H&E slide images, wherein the training dataset of digitized H&E slide images comprises a plurality of digitized H&E training slide images of AA patients, wherein each of the digitized H&E training slide images demonstrates tissue from a uterus of a corresponding AA patient and a portion of a gynecologic tumor of the corresponding AA patient; defining an AA tumor region for each of the digitized H&E training slide images, wherein each of the AA tumor regions comprises a corresponding plurality of AA cells; defining a boundary for each of the AA cells of each of the corresponding pluralities of AA cells; classifying each of the AA cells as one cell type of a plurality of cell types, wherein the plurality of cell types comprises tumor-infiltrating lymphocytes (TILs), non-lymphocyte cells, and cancer cells; for each corresponding plurality of AA cells, generating one or more clusters of AA stromal TILs and one or more clusters of AA epithelial TILs; for each of the corresponding plurality of AA cells, extracting a first plurality of architectural features from the one or more clusters of AA stromal TILs; for each of the corresponding plurality of AA cells, extracting a second plurality of architectural features from the one or more clusters of AA epithelial TILs; refining the first pluralities of architectural features and the second pluralities of architectural features to a third plurality of architectural features, wherein the architectural features of the third plurality of architectural features are more relevant to predicting overall survival (OS) of the AA patients than the other architectural features of the first pluralities of architectural features and the second pluralities of architectural features; generating risk scores for the AA patients, respectively, wherein each of the risk scores for the AA patients is generated based on the third plurality of architectural features of a corresponding digitized H&E slide image of an AA patient of the plurality of digitized H&E training slide images; and training a machine learning classifier based on the risk scores for the AA patients, wherein the machine learning classifier is trained to predict a difference between an aggressive subtype of endometrial cancer (EC) and a non-aggressive subtype of EC.

In some embodiments, the third plurality of architectural features comprises architectural features from only the first plurality of architectural features.

In some embodiments, the operation further comprise: accessing a digitized H&E slide image of an AA patient of interest (POI), wherein the digitized H&E slide image of the AA POI indicates the AA POI has EC, and wherein the digitized H&E slide image of the AA POI demonstrates tissue from a uterus of the AA POI and at least a portion of a gynecologic tumor; defining a tumor region in the digitized H&E slide image of the AA POI, wherein the tumor region comprises a plurality of AA POI cells; defining a boundary for each of the plurality of AA POI cells; classifying each of the plurality of AA POI cells as one cell type of the plurality of cell types; generating one or more clusters of AA POI stromal TILs; extracting the third plurality of architectural features from the one or more clusters of AA POI stromal TILs; generating a risk score for the AA POI based on the third plurality of architectural features that were extracted from the one or more clusters of AA POI stromal TILs; providing the risk score for the AA POI to the machine learning classifier; receiving, from the machine learning classifier, a classification of the EC of the AA POI into either the aggressive subtype of EC or the non-aggressive subtype of EC; and displaying the classification of the EC of the AA POI.

Examples herein can include subject matter such as an apparatus, including an NSCLC immunotherapy response prediction apparatus or system, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting NSCLC immunotherapy response, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method, comprising:
    accessing a digitized hematoxylin and eosin stained slide (H&E slide) image of an African American (AA) patient, wherein the digitized H&E slide image of the AA patient demonstrates one or more indicators of endometrial cancer (EC), and wherein the digitized H&E slide of the AA patient demonstrates tissue from a uterus of the AA patient and at least a portion of a gynecologic tumor;
    defining a tumor region in the digitized H&E slide image, wherein the tumor region comprises at least a part of the portion of the gynecologic tumor, and wherein the tumor region comprises a plurality of individual cells;
    defining a boundary for each of the plurality of individual cells;
    classifying the plurality of individual cells into cell types, wherein the cell types comprise tumor-infiltrating lymphocytes (TILs), non-lymphocyte cells, and cancer cells;
    classifying the TILs as stromal TILs or epithelial TILs;
    generating a cluster of stromal TILs, wherein the cluster of stromal TILs comprises a subset of stromal TILs that are related to one another based on proximity;
    extracting a first plurality of architectural features from the digitized H&E slide image of the AA patient, wherein each of the first plurality of architectural features are at least partially based on the cluster of stromal TILs;
    generating a risk score for the AA patient based on the first plurality of architectural features, wherein the risk score is prognostic of overall survival (OS) of the AA patient;

generating a risk group classification for the AA patient, wherein generating the risk group classification comprises classifying the AA patient into either a high risk group or a low risk group based on the risk score, wherein the high risk group indicates a probability that the AA patient will die within a date range is greater than a threshold probability, and wherein the low risk group indicates the probability that the AA patient will die within the date range is less than or equal to the threshold probability; and displaying the risk group classification of the AA patient.

2. The method of claim 1, further comprising:

providing the risk score to a machine learning classifier that is trained to predict a response of the AA patient to a treatment plan for the EC;

receiving, from the machine learning classifier, a classification of the AA patient into either a responder group (RG) or a non-responder group (NRG), where the NRG indicates the AA patient will not respond to the treatment plan and the RG indicates that the AA patient will respond to the treatment plan; and displaying the classification of the AA patient as either in the NRG or in the RG.

3. The method of claim 2, wherein the treatment plan comprises at least one of chemotherapy and radiation.

4. The method of claim 1, further comprising:

extracting a second plurality of architectural features from the digitized H&E slide image of the AA patient, wherein each of the second plurality of architectural features are at least partially based on the cluster of stromal TILs; and selecting a subset of architectural features of the second plurality of architectural features, wherein the subset of architectural features of the second plurality of architectural features are more relevant to predicting OS of AA patients with EC than the other architectural features of the second plurality of architectural features for a predefined feature selection process, and wherein the subset of architectural features defines the first plurality of architectural features.

5. The method of claim 4, wherein selecting the subset of architectural features of the second plurality of architectural features comprises:

performing a least absolute shrinkage and selection operator (LASSO) technique on the second plurality of architectural features.

6. The method of claim 4, wherein the first plurality of architectural features are based only on the cluster of stromal TILs.

7. The method of claim 1, wherein generating the risk score for the AA patient based on the first plurality of architectural features comprises:

assigning a value to each of the architectural features of the first plurality of architectural features;

assigning a weighting coefficient to each of the values; and combining the values and their respective weighting coefficients linearly to generate the risk score.

8. The method of claim 1, wherein the cluster of stromal TILs is generated via a graph theory technique.

9. The method of claim 1, wherein classifying the AA patient into either the high risk group or the low risk group comprises comparing the risk score of the AA patient to a threshold value.

10. The method of claim 9, wherein classifying the AA patient into either the high risk group or the low risk group further comprises:

classifying the AA patient into the high risk group if the risk score for the AA patient is greater than the threshold value; and classifying the AA patient into the low risk group if the risk score for the AA patient is less than or equal to the threshold value.

11. A non-transitory computer-readable storage device storing computer-executable instructions that when executed cause a processor to perform operations, the operations comprising:

accessing a digitized hematoxylin and eosin stained slide (H&E slide) image of an (AA) African American patient, wherein the digitized H&E slide image of the AA patient demonstrates one or more indicators of endometrial cancer (EC), and wherein the digitized H&E slide image of the AA patient demonstrates tissue from a uterus of the AA patient and at least a portion of a gynecologic tumor;

defining a tumor region in the digitized H&E slide image of the AA patient, wherein the tumor region comprises at least a part of the portion of the gynecologic tumor, and wherein the tumor region comprises a plurality of individual cells;

classifying the plurality of individual cells into cell types, wherein the cell types comprise tumor-infiltrating lymphocytes (TILs) and non-lymphocyte cells;

classifying the TILs as intratumoral TILs or stromal TILs;

generating one or more clusters of stromal TILs, wherein each of the one or more clusters of stromal TILs comprises a subset of stromal TILs that are related to one another based on proximity;

extracting a plurality of architectural features from the digitized H&E slide image of the AA patient, wherein the plurality of architectural features are at least partially based on the one or more clusters of stromal TILs;

generating a risk score for the AA patient based on the plurality of architectural features, wherein the risk score is prognostic of overall survival (OS) of the AA patient;

providing the risk score to a machine learning classifier that is trained to predict whether the EC of the AA patient is either an aggressive subtype of EC or a non-aggressive subtype of EC;

receiving, from the machine learning classifier, a classification of the EC of the AA patient as either the aggressive subtype of EC or the non-aggressive subtype of EC; and displaying the classification of the EC of the AA patient.

12. The non-transitory computer-readable storage device of claim 11, wherein:

each of the plurality of architectural features corresponds to a different architectural feature of the one or more clusters of stromal TILs.

13. The non-transitory computer-readable storage device of claim 12, wherein generating the risk score comprises:

assigning a plurality of values to the plurality of architectural features, respectively, wherein each of the values of the plurality of values corresponds to a number of times a corresponding architectural feature of the plurality of architectural features is present in the digitized H&E slide image of the AA patient; and combining, linearly, the plurality of values with a plurality of weighting coefficients, wherein the plurality of weighting coefficients are attached to the plurality of values, respectively.

14. The non-transitory computer-readable storage device of claim 13, wherein the plurality of architectural features comprises at least four architectural features.

15. The non-transitory computer-readable storage device of claim 14, wherein the plurality of architectural features are based only on the one or more clusters of stromal TILs.

16. The non-transitory computer-readable storage device of claim 15, wherein the plurality of architectural features consists of four architectural features.

17. The non-transitory computer-readable storage device of claim 11, wherein generating the one or more clusters of stromal TILs comprises:
grouping the stromal TILs into corresponding clusters of the one or more clusters of stromal TILs based on a distance in which the stromal TILs are spaced from one another, wherein each stromal TIL of a given cluster of the one or more clusters of stromal TILs is spaced from a neighboring stromal TIL of the given cluster by less than a threshold distance.

18. A non-transitory computer-readable storage device storing computer-executable instructions that when executed cause a processor to perform operations, the operations comprising:
accessing a training dataset of digitized hematoxylin and eosin stained slide (H&E slide) images, wherein the training dataset of digitized H&E slide images comprises a plurality of digitized H&E training slide images of AA patients, wherein each of the digitized H&E training slide images demonstrates tissue from a uterus of a corresponding AA patient and a portion of a gynecologic tumor of the corresponding AA patient;
defining an AA tumor region for each of the digitized H&E training slide images, wherein each of the AA tumor regions comprises a corresponding plurality of AA cells;
defining a boundary for each of the AA cells of each of the corresponding pluralities of AA cells;
classifying each of the AA cells as one cell type of a plurality of cell types, wherein the plurality of cell types comprises tumor-infiltrating lymphocytes (TILs), non-lymphocyte cells, and cancer cells;
for each corresponding plurality of AA cells, generating one or more clusters of AA stromal TILs and one or more clusters of AA epithelial TILs;
for each of the corresponding plurality of AA cells, extracting a first plurality of architectural features from the one or more clusters of AA stromal TILs;
for each of the corresponding plurality of AA cells, extracting a second plurality of architectural features from the one or more clusters of AA epithelial TILs;
refining the first plurality of architectural features and the second plurality of architectural features to a third plurality of architectural features, wherein the architectural features of the third plurality of architectural features are more relevant to predicting overall survival (OS) of the AA patients than the other architectural features of the first plurality of architectural features and the second plurality of architectural features;
generating risk scores for the AA patients, respectively, wherein each of the risk scores for the AA patients is generated based on the third plurality of architectural features of a corresponding digitized H&E slide image of an AA patient of the plurality of digitized H&E training slide images; and
training a machine learning classifier based on the risk scores for the AA patients, wherein the machine learning classifier is trained to predict a difference between an aggressive subtype of endometrial cancer (EC) and a non-aggressive subtype of EC.

19. The non-transitory computer-readable storage device of claim 18, wherein the third plurality of architectural features comprises architectural features from only the first plurality of architectural features.

20. The non-transitory computer-readable storage device of claim 18, wherein the operations further comprise:
accessing a digitized H&E slide image of an AA patient of interest (POI), wherein the digitized H&E slide image of the AA POI indicates the AA POI has EC, and wherein the digitized H&E slide image of the AA POI demonstrates tissue from a uterus of the AA POI and at least a part of the portion of a gynecologic tumor of the AA POI;
defining a tumor region in the digitized H&E slide image of the AA POI, wherein the tumor region comprises a plurality of AA POI cells;
defining a boundary for each of the plurality of AA POI cells;
classifying each of the plurality of AA POI cells as one cell type of the plurality of cell types;
generating one or more clusters of AA POI stromal TILs;
extracting the third plurality of architectural features from the one or more clusters of AA POI stromal TILs;
generating a risk score for the AA POI based on the third plurality of architectural features that were extracted from the one or more clusters of AA POI stromal TILs;
providing the risk score for the AA POI to the machine learning classifier;
receiving, from the machine learning classifier, a classification of the EC of the AA POI into either the aggressive subtype of EC or the non-aggressive subtype of EC; and
displaying the classification of the EC of the AA POI.

\* \* \* \* \*

UNITED STATES PATENT AND TRADEMARK OFFICE
CERTIFICATE OF CORRECTION

PATENT NO. : 12,073,560 B2  
APPLICATION NO. : 17/671882  
DATED : August 27, 2024  
INVENTOR(S) : Anant Madabhushi et al.

Page 1 of 1

It is certified that error appears in the above-identified patent and that said Letters Patent is hereby corrected as shown below:

In the Specification

Column 1, Lines 14 through 22, under Federal Funding Notice; please replace "This invention was made with government support under CA199374, CA249992, CA202752, CA208236, CA216579, CA220581, CA239055. CA248226, CA254566, HL151277, EB028736, RR012463, and TR000254 awarded by the National Institutes of Health; and W81XWH-19-1-0668, W81XWH-15-1-0558, W81XWH-20-1-0851, W81XWH-18-1-0440, W81XWH-20-1-0595, and W81XWH-18-1-0404 awarded by the Department of Defense. The government has certain rights in the invention." With --This invention was made with government support under CA199374, CA249992, CA202752, CA208236, CA216579, CA220581, CA239055, CA248226, CA254566, HL151277, EB028736, RR012463, and TR000254 awarded by the National Institutes of Health; W81XWH-19-1-0668, W81XWH-15-1-0558, W81XWH-20-1-0851, W81XWH-18-1-0440, and W81XWH-18-1-0404 awarded by the Department of Defense. The government has certain rights in the invention.--

Signed and Sealed this  
Twelfth Day of November, 2024

Katherine Kelly Vidal  
*Director of the United States Patent and Trademark Office*